(12) United States Patent
Cuzick et al.

(10) Patent No.: US 6,351,666 B1
(45) Date of Patent: Feb. 26, 2002

(54) METHOD AND APPARATUS FOR SENSING AND PROCESSING BIOPOTENTIALS

(75) Inventors: Jack A. Cuzick, Richmond (GB); Richard J. Davies, Saddle River, NJ (US); John D. Stephens, Alpharetta, GA (US); Vera Borgwardt; Craig M. Housworth, both of Roswell, GA (US); Xingye Lei, Richland, WA (US); Peter D. Gadsby, Cumming, GA (US); Abe Iskac, Duluth, GA (US)

(73) Assignee: Biofield Corp., Alpharetta, GA (US)

( * ) Notice: Subject to any disclaimer, the term of this patent is extended or adjusted under 35 U.S.C. 154(b) by 0 days.

(21) Appl. No.: 09/256,294

(22) Filed: Feb. 24, 1999

Related U.S. Application Data

(60) Provisional application No. 60/076,353, filed on Feb. 27, 1998, provisional application No. 60/080,775, filed on Apr. 6, 1998, and provisional application No. 60/094,643, filed on Jul. 30, 1998.

(51) Int. Cl.[7] .................................................. A61B 5/05
(52) U.S. Cl. ........................ 600/547; 600/382; 600/301; 128/920; 128/925
(58) Field of Search .................................. 600/547, 301, 600/393, 407, 382; 706/15, 38, 48; 128/920, 925, 922

(56) References Cited

U.S. PATENT DOCUMENTS

| 4,328,809 A | 5/1982 | Hirschowitz et al. ........ 128/653 |
| 4,407,300 A | 10/1983 | Davis ......................... 128/734 |
| 4,416,288 A | 11/1983 | Freeman ..................... 128/731 |
| 4,486,835 A | 12/1984 | Bai et al. ..................... 364/414 |
| 4,557,271 A | 12/1985 | Stoller et al. ................ 128/734 |
| 4,557,273 A | 12/1985 | Stoller et al. ................ 128/738 |
| 4,955,383 A | 9/1990 | Faupel ......................... 128/653 |
| 5,099,844 A | 3/1992 | Faupel ....................... 128/653.1 |
| 5,697,369 A | 12/1997 | Long, Jr. et al. .......... 128/65.31 |
| 5,715,821 A | 2/1998 | Faupel ....................... 128/653.1 |
| 6,179,786 B1 * | 1/2001 | Young ......................... 600/549 |

* cited by examiner

Primary Examiner—Marvin M. Lateef
Assistant Examiner—Eleni Mantis Mercader
(74) Attorney, Agent, or Firm—Nixon Peabody LLP; Daniel W. Sixbey

(57) ABSTRACT

In accordance with the apparatus and method of the present invention, a biopotential lesion sensor is placed directly over a lesion in a symptomatic breast and a reference sensor is located away from the symptomatic breast. A plurality of electropotential test measurements are taken during a test period with the lesion sensor and averaged to obtain a primary test potential. This primary test potential can be weighted to compensate for one or more biologic variables such as patient age, time in the patient menstrual cycle, and the time of day during which the measurement is taken. To provide noise enhancement of the primary test potential average measurement, the symptomatic breast is divided into four equal quadrants with one quadrant containing the lesion. One, two or all three of the remaining three non-lesion quadrants is provided with at least one non-lesion test sensor, and during the test period a number of electropotential measurements equal to those taken by the sensor over the lesion are taken and averaged. The processor may then obtain the median value of the averages for the non-lesion quadrants or alternatively the mean value, and it will then subtract this median or mean value from the primary test potential to provide the differential value.

95 Claims, 9 Drawing Sheets

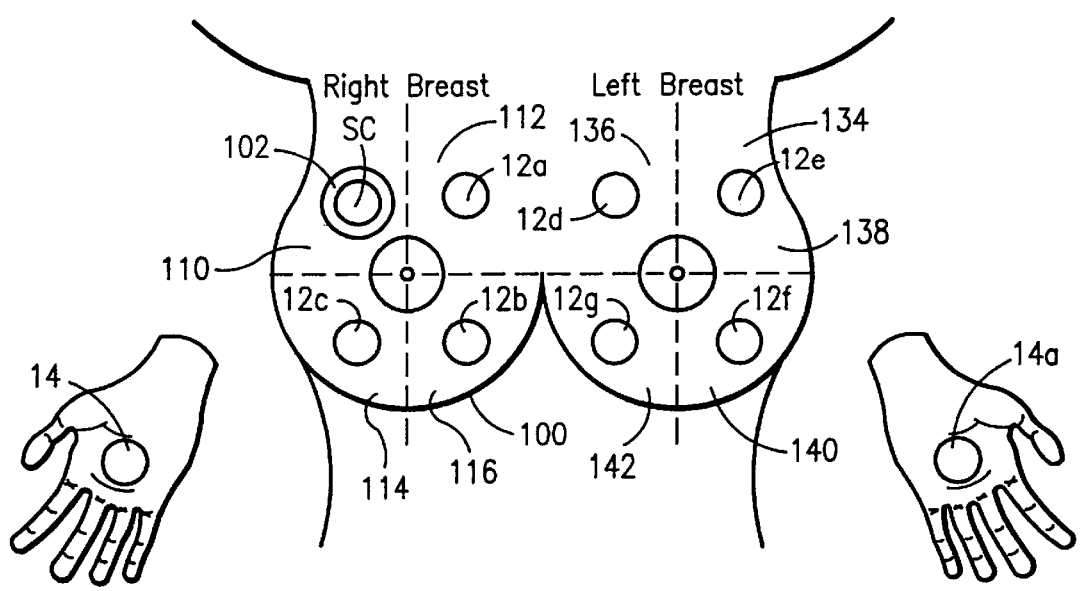
FIG. 8
FIG. 9
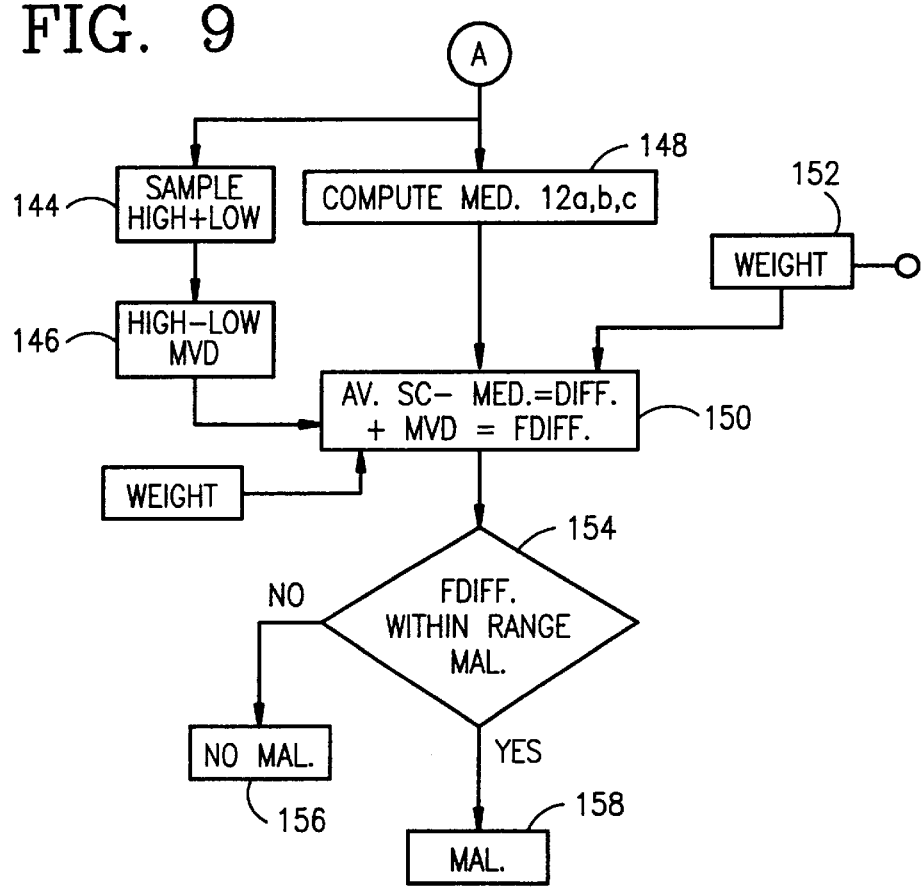

METHOD AND APPARATUS FOR SENSING AND PROCESSING BIOPOTENTIALS

This application is a continuation-in-part application of provisional applications Serial No. 60/076,353 filed Feb. 27, 1998, 60/080,775 filed Apr. 6, 1998, and 60/094,643 filed Jul. 30, 1998.

BACKGROUND OF THE INVENTION

A breast cancer investigation is usually triggered by the discovery of a breast mass, and although in many instances the mass is the result of a benign lesion, this is not discovered until a patient has often undergone a battery of diagnostic tests which are sometimes invasive. A need exists for a noninvasive, adjunctive method and device which will aid a physician in making a clinical decision as to whether or not additional diagnostic tests for breast cancer are warranted.

Breast cancer is thought to originate from epithelial cells in the terminal ductal lobular units of mammary tissue. The development of breast cancer results in regions of epithelial electrical depolarization within the breast parenchyma, which led to the theory that the measurement of skin surface electropotentials would provide data to indicate the presence of underlying abnormal proliferation indicative of cancer. Many methods and devices have been developed in an attempt to implement this theory.

For example, U.S. Pat. No. 4,328,809 to B. H. Hirschowitz et al. deals with a device and method for detecting the potential level of the electromagnetic field present between a reference point and a test point on a living organism. Here, a reference electrode provides a first signal indicative of the potential level of the electromagnetic field at the reference point, while a test electrode provides a second signal indicative of the potential level of the electromagnetic field at the test point. These signals are provided to an analog-to-digital converter which generates a digital signal as a function of the potential difference between the two, and a processor provides an output signal indicative of a parameter or parameters of the living organism as a function of this digital signal. For breast cancer detection, Hirschowitz et al. shows that a test electrode can be placed in each quadrant of a human female breast and that multiple measurements can be taken during a test period with each test electrode and a reference electrode. These multiple measurements are digitized, normalized, and summed to provide an average or mean output signal indicative of a parameter of the living organism under test.

Similar biopotential measuring devices are shown by U.S. Pat. No. 4,407,300 to Davis, and U.S. Pat. No. 4,557,271 and 4,557,273 to Stoller et al. Davis in particular discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al. patent contemplates the use of a plurality of test electrodes, while U.S. Pat. No. 4,416,288 to Freeman and U.S. Pat. No. 4,486,835 to Bai disclose the use of measuring electrode arrays.

Unfortunately, these previous methods for employing biopotentials measured at the surface of a living organism as an adjunctive aid to diagnosis, while basically valid, are predicated upon an overly simplistic hypothesis which is not effective for many disease states. The prior methods and devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to inaccuracy, particularly where only surface measurements are taken.

U.S. Pat. Nos. 4,955,383 and 5,099,844 to M. L. Faupel disclose a method and apparatus using electropotential differentials between averaged values provided by a plurality of different sensors. This method operates on the basis that maximum differentials between areas of diseased tissue and apparently normal tissue in other areas of a breast for a breast cancer investigation provide informative parameters not subject to the inaccuracy of previous methods.

Still, the accurate measurement of DC biopotentials for sensing disease, such as breast cancer, is very difficult to accomplish, for the DC potentials to be sensed are of a very low amplitude. Due to factors such as the low DC potentials involved and the innate complexity of biological systems, the collected data signals tend to include a substantial amount of noise which makes accurate analysis difficult. Also, biological systems are notorious for their complexity, nonlinearity and nonpredictability, and wide variations from the norm are not uncommon. Thus it is necessary to develop a method and apparatus for obtaining the necessary data from the measurement of biopotentials and then to extract and analyze pertinent information which is relevant to a condition under study.

In an attempt to accomplish this, the method and apparatus of the previous Faupel patents was combined with one or more preprogrammed neural networks as illustrated by U.S. Pat. No. 5,697,369 to D. M. Long Jr et al. and U.S. Pat. No. 5,715,821 to M. L. Faupel. With a neural network, data can be processed by several layers of interacting decision points or neurons. The network must be taught to recognize patterns from input data to produce a predictive output, and this can prove to be a complex and often time consuming process involving many variables. Therefore, a need has arisen for a simple method and apparatus for use in the analysis of female breast electropotentials to minimize the effects of noise on the measurement data and to compensate for the biologic variability which affects the measurement data. Past methods and devices have concentrated on developing accurate data from sensed biopotentials which will provide an indication of the probability that a malignancy exists. These methods have ignored the effects of various biologic variables such as menstrual status or timing of the menstrual cycle. (Electrical Potential Measurements in Human Breast Cancer and Benign Lesions; Tumor Biology, 1994, pages 147–152). However, in younger women (ages 18–56) with a palpable breast mass, the prevalence of cancer becomes lower as age decreases. The sensitivity of mammography is limited in this less than 56 age group due to the density of breast tissue. Because of this, a considerable degree of diagnostic uncertainty remains after physical examination and mammography, and as a result, the open biopsy procedure performed on women in this 56 year or under population yields a low percentage of malignancy diagnoses. Physicians dealing with breast cancer detection have a need for a noninvasive technique which will provide data to effectively aid them in reaching a clinical decision that a suspicious lesion is benign and does not require a breast biopsy while still providing an indication that malignancy is probable when such is the case so that a decision can be made to conduct a biopsy.

SUMMARY OF THE INVENTION

It is a primary object of the present invention to provide a novel and improved method and apparatus for sensing and processing electropotentials from a female breast which minimizes the effects of noise on the measurement data.

Another object of the present invention is to provide a novel and improved method and apparatus for sensing and processing electropotentials from a human subject which involves weighting the measured electropotentials to compensate for biologic variables.

A further object of the present invention is to provide a novel and improved method and apparatus for sensing and processing electropotentials from a human subject which involves weighting the measured electropotentials in accordance with the age of the subject.

Yet another object of the present invention is to provide a novel and improved method and apparatus for sensing and processing electropotentials from a female breast which involves weighting and/or discarding the electropotential measurement in response to the dates of menses and/or hormonal levels.

A further object of the present invention is to provide a novel and improved method and apparatus for sensing and processing electropotentials from a female breast where a primary electropotential measurement is obtained from an area of a symptomatic breast which is directly over a lesion and this primary electropotential measurement is processed with an electropotential measurement obtained from one or more areas of the symptomatic breast which are spaced from the lesion to provide noise reduction.

Yet a further object of the present invention is to provide a novel and improved method and apparatus for sensing and processing electropotentials from a female breast where a primary electropotential measurement is obtained from an area of a symptomatic breast which is directly over a lesion and this primary electropotential measurement is processed with electropotential measurements obtained from one or more areas of the symptomatic breast which are spaced from the lesion and from areas of the asymptomatic breast which correspond with the areas of the symptomatic breast where measurements are taken to reduce noise.

Another object of the present invention is to provide a novel and improved method and apparatus for sensing and processing electropotentials from a female breast which involves weighting the measured electropotentials to compensate for biologic variables which include one or more of patient age, hormonal levels, time in the patient menstrual cycle, and time of day during which the measurement is taken.

These and other objects of the present invention are accomplished by the apparatus and method of the present invention. In the most basic mode of operation, a biopotential sensor is placed directly over a lesion in a symptomatic breast, a reference sensor is located either away from the symptomatic breast, or directly over the nipple of the symptomatic breast, and a plurality of electropotential test measurements are taken during a test period and averaged to obtain a primary test potential. This primary test potential can be weighted to compensate for one or more biologic variables such as patient age, hormonal levels, time in the patient menstrual cycle, and the time of day during which the measurement is taken. These biologic variables are provided to a processor for the apparatus by one or more data input devices which can include a keyboard and possibly sensors for some biologic conditions. The processor stores weighting factors for each biologic variable and various levels of the biologic variable, and applies one or more of these weighting factors to the primary test potential measurement which is then displayed or compared to a reference value and the result displayed. For some period of a female menstrual cycle, the processor will either prevent the display and will instead provide an indication that no accurate measurement can be taken, or will weight the measurement taken to compensate for the period during the menstrual cycle when the measurement is obtained.

To provide noise enhancement of the primary test potential average measurement, the symptomatic breast is divided into four equal quadrants with one quadrant containing the lesion. At least one of the remaining three non-lesion quadrants is provided with a biopotential sensor, and during the test period a number of electropotential measurements equal to those taken by the sensor over the lesion are taken and averaged. This average value from the non-lesion quadrant is subtracted from the primary test potential average to provide a differential value which then can be compared to a predetermined reference value and the result displayed. Often both the average from the non-lesion quadrant and the primary test potential average are weighted before the subtraction step by the processor to obtain the differential. Also, the processor will often provide additional weighting for biologic variables.

Further enhanced noise reduction of the primary test potential average measurement is obtained by placing at least one biopotential sensor in each non-lesion quadrant of the breast and taking the same number of electropotential test measurements during a test period from each non-lesion quadrant that are taken with the sensor over the lesion. At the end of the test period, the processor averages the measurements taken by each sensor to obtain an average, and the average for the sensor over the lesion constitutes the primary test potential. The processor may then obtain the median value of the averages for the non-lesion quadrants or alternatively the mean value, and it will then subtract this median or mean value from the primary test potential to provide the differential value. Again the mean or median value and the primary test potential may be weighted before the subtraction and additional weighting may be provided for biologic variables. The resultant differential value is then compared to a predetermined reference value.

Maximum noise reduction of the primary test potential average is obtained as described above using averages obtained from the biopotential sensors over the non-lesion quadrants of the symptomatic breast. Also mirror image sensors are arranged on the asymptomatic breast to duplicate the positions of the sensors on the symptomatic breast. During a test period, the processor causes all sensors to take the same number of plural electropotential measurements, and at the end of the test period the average value of the measurements for each individual channel is computed.

For the symptomatic breast, the processor computes either the median or the mean value for the non-lesion quadrants. For the asymptomatic breast, the processor computes a maximum voltage differential value (MVD) which is the difference value obtained by subtracting the lowest average value obtained for the asymptomatic breast from the highest average value. Then the processor subtracts the median or mean value for the non-lesion quadrants of the symptomatic breast from the primary test potential average and adds the MVD from the asymptomatic breast to obtain a differential value which is compared to a predetermined reference.

Alternatively, instead of the MVD from the asymptomatic breast, the processor may obtain a median value or a mean value from the averages for the asymptomatic breast and add these to the result of the subtraction of values for the symptomatic breast. Again, all values from the symptomatic and asymptomatic breast may be weighted and additional weighting may be provided for biologic variables.

For screening purposes, at least one sensor may be placed in each breast quadrant and multiple measurements taken with each sensor and averaged to obtain a quadrant average value for each quadrant. The average values are compared, and if a quadrant average value varies from the others by more than a predetermined amount, this quadrant is designated as a potential lesion quadrant.

BRIEF DESCRIPTION OF THE DRAWINGS

FIG. 8 is a diagram showing a third sensor placement method of the present invention;

FIG. 9 is a flow diagram illustrating the operation of the apparatus of FIG. 1 with the sensor placement of FIG. 8;

DETAILED DESCRIPTION OF THE INVENTION

Figure 1:
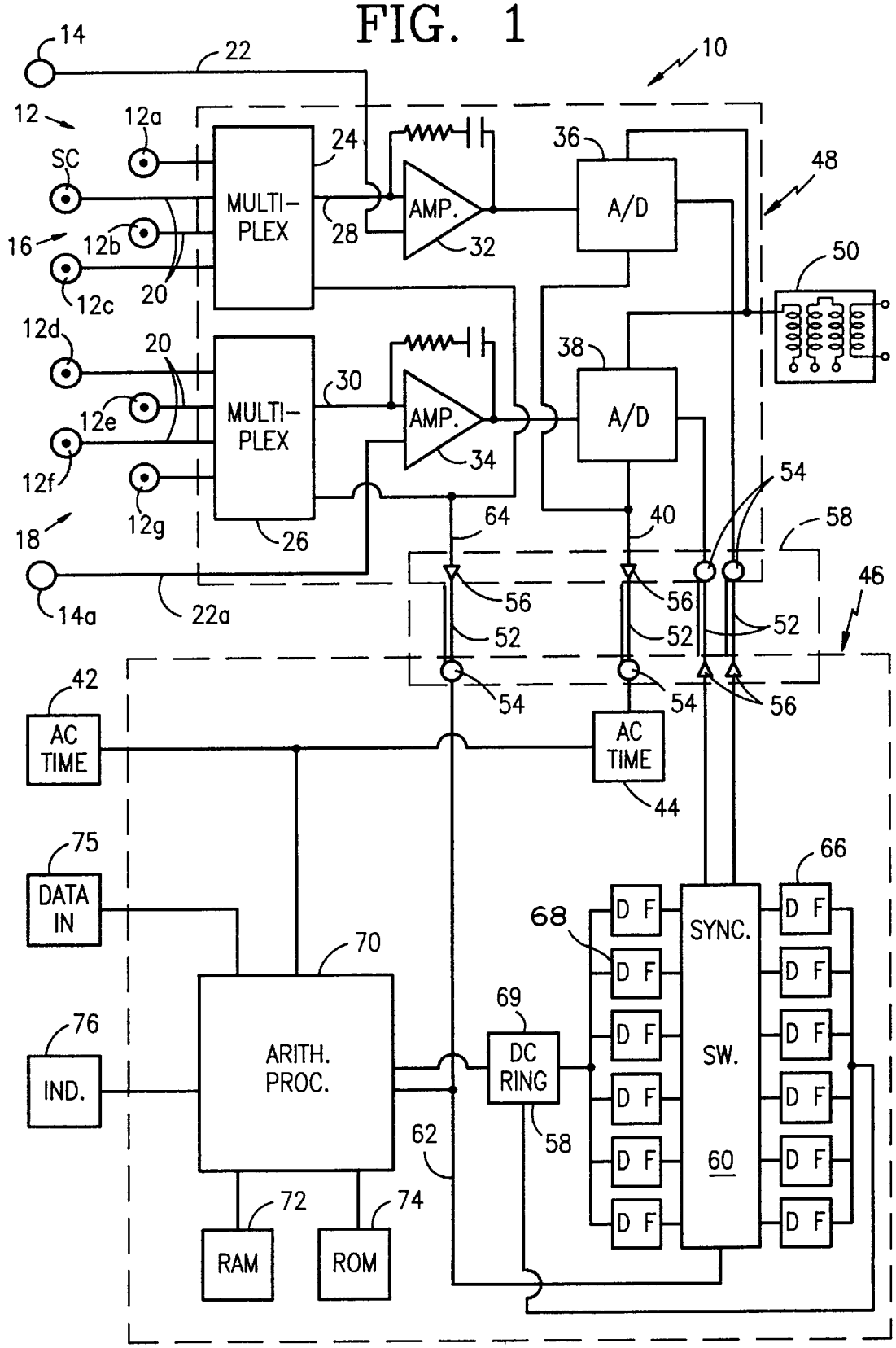
FIG. 1 is a block diagram of the apparatus of the present invention.
Figure 14:
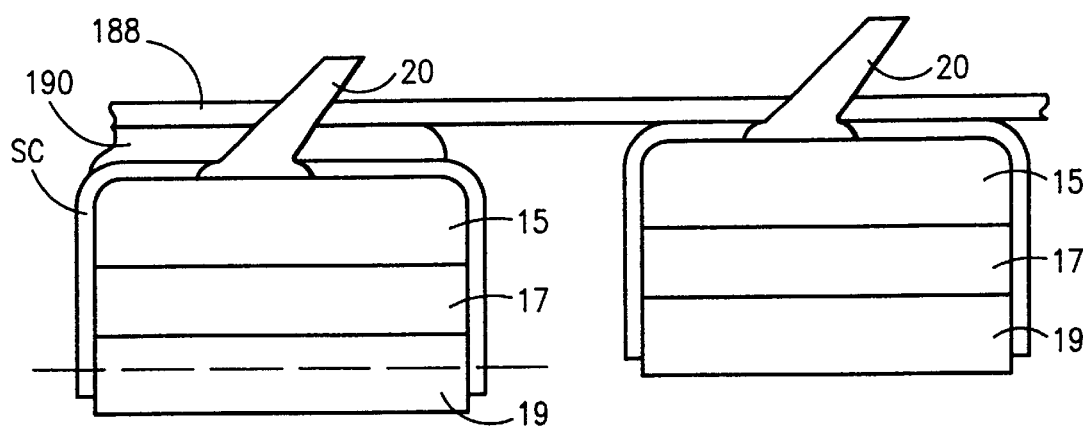
FIG. 14 is a sectional diagram of two biopotential sensors and a unique sensor mount.

FIG. 1 discloses a basic block diagram of the apparatus of the present invention indicated generally at 10 for evaluating skin surface electropotentials associated with suspicious breast lesions prior to a complete diagnostic workup. To accomplish this, a plurality of DC biopotential test sensors for sensing DC electropotentials, such as sensing electrodes 12 and at least two reference sensors such as electrodes 14 and 14a are used to provide analog outputs indicative of DC electropotentials measured on the breasts of a human female subject. When sensing electrodes form the sensors 12 and 14, 14a, they may include a layer of silver 15 forming an electrode, a layer of silver chloride 17, and an ion conducting cream or gel 19 as shown in FIG. 14 (see also U.S. Pat. Nos. 5,660,177 and 5,823,957).

The method of this invention contemplates the uses of a variety of different sensor arrays depending upon the intended application for which the device 10 is used. The aim is to measure the areas of electrical activity which occur as a function of the underlying biological activity of the organ system. The number of sensors, such as sensing electrodes 12 used in the measurement will also be a function of the specific application.

In FIG. 1 for purposes of illustration, two sensor arrays 16 and 18 are shown with each array consisting of four sensors 12 providing four separate output channels for each array. In actual practice, for some applications, each array will contain more sensors as will be described.

The sensors 12 of the sensor arrays 16 and 18 should be mounted in a manner which permits the sensors to be accurately positioned against the curved surface of the skin of a subject in the area of a test site while still maintaining spacing and the position of the sensors in a predetermined pattern to be described. The sensors 12 and reference sensors 14 and 14a must all be of a type suitable for detecting DC electropotentials indicative of the potential level present in the breasts of a female subject. These sensors should be of a type which do not cause a substantial battery effect between the breasts under test and the sensors and must have a very low DC offset potential. (See U.S. Pat. Nos. 5,217, 014, 5,560,357, 5,660,177 and 5,823,957).

The device 10 is a multi-channel device having leads 20 extending separately from the sensors 12 in each array and leads 22 and 22a extending from the reference sensors 14 and 14a respectively. Each sensor 12 in combination with a reference sensor forms a separate data channel which transmits one or more analog signals indicative of the DC electropotential at a specific site on the breast. The leads 20 from the array 16 are connected to a solid state multiplexor 24, while the leads from the sensor array 18 are connected to a second solid state multiplexor 26. Each sensor array connected to the device 10 provides a plurality of outputs to a multiplexor connected to the array, and this multiplexor switches between the leads 20 during a test period to connect the analog signals on each lead sequentially to a multiplexor output such as the output lines 28 and 30 to create a time division multiplexed output. By providing a high speed solid state multiplexor for each array, it is possible to repeatedly sample electropotentials from each of the plurality of sensors in an array during a test period of minimal duration.

In the device 10 of the present invention, the analog signals on the outputs from each multiplexor are passed through separate relatively high frequency low pass filter amplifiers, such as the filter amplifiers 32 and 34. These filter amplifiers have a relatively high cutoff frequency of 40 Hertz or more, and thus require a stabilization period with analog signals of the amplitude provided on the output lines 28 and 30 to the filters.

The analog output signals from the filter amplifier 32 connected to the multiplexor for the sensor array 16 are directed to an analog to digital converter 36, while the analog output signals from the filter amplifier 34 for the sensor array 18 are connected to an analog to digital converter 38. The analog to digital converters operate to convert the input analog signals to output digital signals which are a function of the analog inputs.

The analog to digital converters 36 and 38 operate in response to timing signals provided on a timing line 40 which synchronize the conversions with the line frequency of the AC power line 42 for the device 10. The AC line frequency is a large source of noise which adversely affects the biopotential signals sensed by the device, and this line frequency noise is minimized by synchronizing the analog to digital conversions with the line frequency. To accomplish this, an AC timer section 44 in a central processor unit 46 senses the AC power line frequency and provides four timing pulses on the timing line 40 at equal positions A, B, C and D on the sine wave for the AC line cycle. The timing pulses occur equal distances from the peak or 90° point of each half cycle and on opposite sides thereof. Ideally, these timing pulses occur at points on the half cycle which are 90° from the peak point. Thus, a timing pulse is provided at an equal position on the rise and fall curve of each half cycle, causing a conversion to occur in response to each timing pulse. Noise generated during the rise portion of the half cycle tends to be cancelled by noise generated during the fall portion.

The multiplexors 24 and 26, the filter amplifiers 32 and 34 and the analog to digital converters 36 and 38 form an isolation section 48 which is electrically connected to a subject by means of the sensor arrays 16 and 18. This isolation section is provided with a lower power dedicated power supply 50 which does not provide power sufficient to cause injury to a subject. The power supply 50 receives AC power from the AC powerline 42 and includes a dual isolation circuit including two transformers between the AC powerline and the isolation section which provide a dual barrier to the AC powerline. The power supply 50 converts the input AC to a low voltage DC which powers the isolation section 48. The isolation section is electrically isolated from the central processor unit 46 which is connected to the AC powerline 42. To achieve this electrical isolation, all signals between the isolation section and the central processor unit may be conducted over optical cables 52 as optical signals. Thus, the timing signals from the AC timer section 44 are converted to light pulses by a conversion unit 54, such as a light emitting diode, transmitted over an optical cable 52 and reconverted to electrical pulses by a reconversion unit 56. Similarly, the electrical digital outputs from the analog to digital converters 36 and 38 are converted to light pulses and transmitted to the central processor 46 where they are reconverted into electrical digital signals. Alternatively, an optoisolator chip shown in broken lines at 58 may replace the optical cables 52, conversion units 54 and reconversion units 56 to convert the electrical signals to optical signals and to accomplish the reconversion. The electrical digital signals from either the reconversion unit 56 or the optoisolator chip 58 are directed to a synchronous switching or de-multiplexor 60.

The de-multiplexor 60 is synchronized with the multiplexors 24 and 26 and provides timing signals on a line 62 which are transmitted as optical signals to the isolation section 48 where they are reconverted to electrical timing signals which are sent over a line 64 to the multiplexors. Digital filter arrays 66 and 68 in the software for the central processing unit include a dedicated digital filter such as two-pole, Infinite Impulse Response (IIR) filter, with a Butterworth response, for each electrode channel in the sensor arrays 16 and 18 respectively. Thus, as the multiplexors 24 and 26 are simultaneously transmitting analog signals from a selected sensor channel in the sensor arrays 16 and 18, the digital signals indicative of these analog signals are being directed by the de-multiplexor to the digital filters in the arrays 66 and 68 which are dedicated to those channels. When the multiplexors switch channels, the de-multiplexor switches to corresponding digital filters.

Filtered digital data from the digital filter arrays 66 and 68 are analyzed by a DC range sensing section 69 of the central processing unit (that is in fact formed by a software program) which is programmed to sense the magnitude of the DC electropotential signals represented by the filtered digital signals. Digital signals indicative of DC signals within a predetermined range of millivolts (for example −200 to +200 millivolts) are accepted while signals outside this millivolt range are rejected as spurious. The accepted signals are directed to processing section 70 of the central processor unit 46 having a RAM memory 72 and a ROM memory 74. This data is stored in memory and is processed by the processing section in accordance with a stored program to perform the condition sensing functions of the present invention. The processing section combines sensed electropotential data with data provided by a data input section 75, which may constitute a keyboard or a keyboard in combination with other data sensing units, all of which provide inputs to the processing section. The output from the processing section is connected to control the display on an indicator unit 76.

It should be understood that for clarity of description, sections of the central processor unit 46 have been illustrated as operative blocks, but these sections may constitute software controlled functions.

With reference to FIGS. 2–13, the operation of the apparatus 10 will be clearly understood from a brief consideration of the steps of the invention which the device is programmed to perform. During a test period initiated by the processing section 70, the electropotential between selected reference sensors 14 and 14a and selected test sensors, such as sensors 12 is measured, converted to a digital signal and stored for processing by the processing section 70. Sequential measurements between the reference sensor and the selected test sensors are taken. In accordance with the method of the present invention, the measurement indications on each individual channel are not averaged with those from other channels, but are instead kept separate and averaged by channel within the processing section 70 at the end of the test period. For the duration of a single test period, for example, from eight measurement channels, the processing section will obtain eight average signals indicative of the average electropotential for the test period between the reference sensors 14 and 14a and each of the test sensors in the sensor arrays 16 and 18. Of course, more reference sensors can be used, although only one reference sensor per array has been shown for purposes of illustration.

Having once obtained an average signal level indication for each channel, the results of the measurements taken at multiple sites are analyzed mathematically to determine the relationships between the average signal values obtained, and these signal values are often weighted for noise reduction and to compensate for biologic variables.

Figure 2:
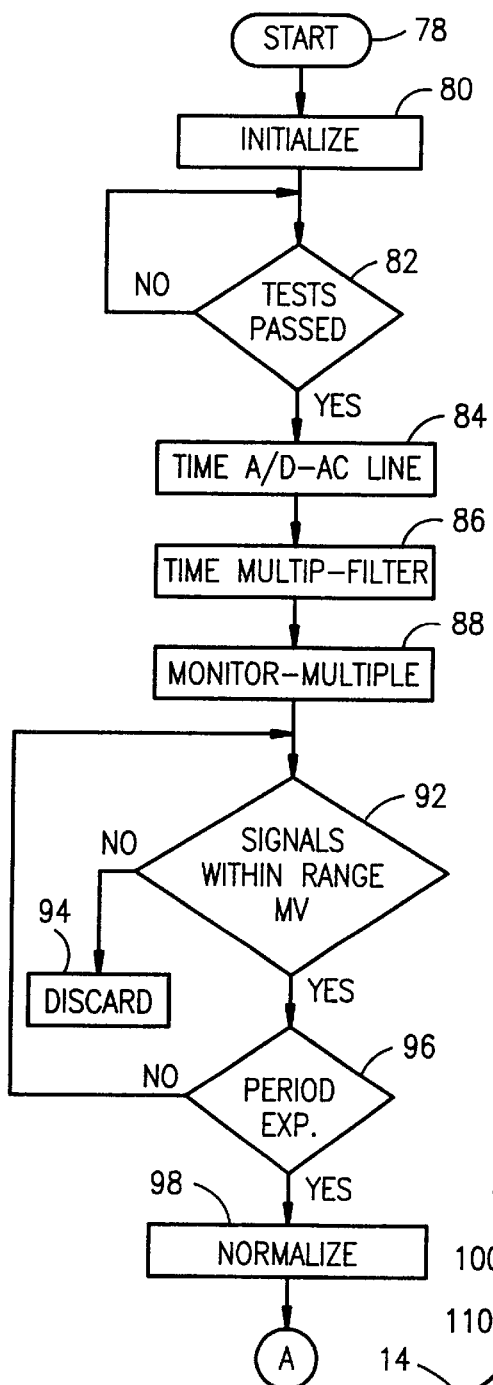
FIG. 2 is a flow diagram illustrating the basic operation of the apparatus of FIG. 1.
Figure 3:
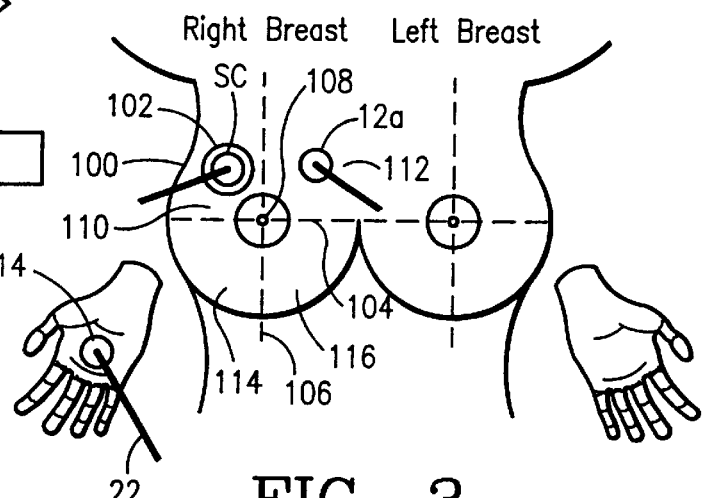
FIG. 3 is a diagram showing a first sensor placement method of the present invention.

The basic measuring operation controlled by the central processing unit 46 will best be understood with reference to the flow diagrams of FIGS. 2 and 3. The operation of the unit 10 is started by a suitable start switch as indicated at 78 to energize the central processing unit 46, and this triggers an initiate state 80. In the initiate state, the various components of the device 10 are automatically brought to an operating mode, with for example, the indicator 76 being activated while various control registers for the central processing unit are reset to a desired state.

Subsequently, a test period is initiated at 82 wherein the various components of the system are tested for proper operability. During this test period, the electrode arrays 16 and 18 may also be tested to make certain that electrodes are being used which accurately measure DC biopotentials.

If all system components test out properly during the system test period, then timing of the analog to digital converters in accordance with the AC line frequency begins at 84 and the timing of the multiplexors and de-multiplexors begins at 86. With the analog to digital converters, multiplexors, de-multiplexors and digital filters in operation, it is now possible to monitor the biopotential signals from one or more test area during a monitoring period begun at 88. During this monitoring period, conditions in the test area contacted by the electrode arrays 16 and 18 are stabilized so that subsequent reliable measurements of DC biopotentials can be obtained. This monitoring period can be an extended time period, for example ten minutes, which is used for all patients and is sufficient to insure stabilization.

During the test period the digitized signals received from the various sequenced channels are monitored at 92 to determine whether or not each biopotential represented by the signals is within a predetermined range of millivolts. Digitized values indicative of DC signals outside this range are discarded at 94 and the remaining signals are used to provide an average or normalized value for each channel. Then, at 96, the central processor unit determines whether the test period has expired and the desired number of measurements have been taken, and if not, the collection of measurement samples or values continues. At the end of the test period, the average value for each channel is obtained at 98 by summing the values obtained for that channel during the test period and dividing the sum by the number of measurements taken. These average values are then processed in the various manners hereinafter described.

As shown in FIGS. 3, 5, 8, 16 and 17, in accordance with the present invention, the symptomatic breast 100 of a patient containing the suspicious lesion 102 is divided into four, equal, imaginary quadrants, one of which contains the lesion. The quadrants are defined by an imaginary horizontal line 104 which is perpendicular to an imaginary vertical line 106, both of which pass through and intersect at the nipple 108 of the symptomatic breast. Sensors from a sensor array, for example the array 16, are intended to be positioned on the symptomatic breast 100, and a lesion test sensor SC of that array provides a primary electropotential value used in the measurement of the present invention. Preferably, the lesion 102 is a palpable lesion so that the sensor SC can be centered directly over the lesion. Although only one sensor per breast quadrant has been shown for illustrative purposes in FIGS. 3, 5, 8, 16 and 17, multiple sensors can be used in each quadrant to provide an electropotential value for that quadrant.

Figure 4:
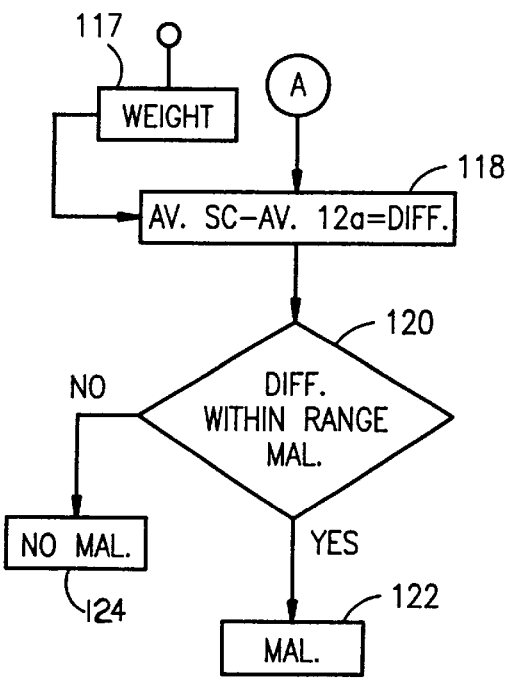
FIG. 4 is a flow diagram illustrating the operation of the apparatus of FIG. 1 with the sensor placement of FIG. 3.

In FIGS. 3 and 4, in accordance with the simplest form of the method and operation of the apparatus of the present invention, only the lesion test sensor SC and one other non-lesion test sensor in the sensor array 16 are used. This second sensor 12a is positioned in a quadrant of the symptomatic breast which is outside of the quadrant 110 containing the suspicious lesion. This could be a horizontally positioned quadrant 112, a vertically positioned quadrant 114, or a diagonally positioned quadrant 116. The reference sensor 14 may be positioned on the skin of the subject remote from the symptomatic breast, such as on the hand or the sub-xyphoid area of the subject, or directly over the nipple of the breast. During a test period, the processor 70 causes the same number of plural measurements to be taken by each of the sensors SC and 12a and an average is obtained at 98 for each sensor. Then, at 118, the processor subtracts the average value for the sensor 12a from the average value for the sensor SC to obtain a differential value. The values used to obtain the differential value may be weighted at 117 in a manner to be described. Then this differential value is compared at 120 with a predetermined reference stored in one of the memories 72 or 74. Preferably the reference is a predictive index developed by stepwise regression using differentials from women with lesions the status of which has been identified to provide a multivariate model. Comparison of the differential value with this predictive index provides predictive information regarding the presence or absence of malignancy. If the differential falls within the malignancy ranges, malignancy is predicted at 122. Conversely, if the differential does not fall within the malignancy range, no malignancy is predicted at 124. Thus the predetermined reference provides the median value in a population predictive of the probability of cancer.

In testing the 55 year and under female population, the device 10 is used to obtain measurements from women with no breast lesions, women with a breast lesion who have been determined not to need biopsy, women with a breast lesion which has been shown by biopsy to be benign, and women who biopsy shows have a malignant breast lesion. The measured electropotentials have been shown to be consistently the highest for women with malignant lesions and consistently lowest for woman with no lesions. Measured electropotentials are higher for woman with lesions who have been determined not to need biopsy than for women with no breast lesions, and still higher for women with a breast lesion which biopsy has shown to be benign.

Figure 5:
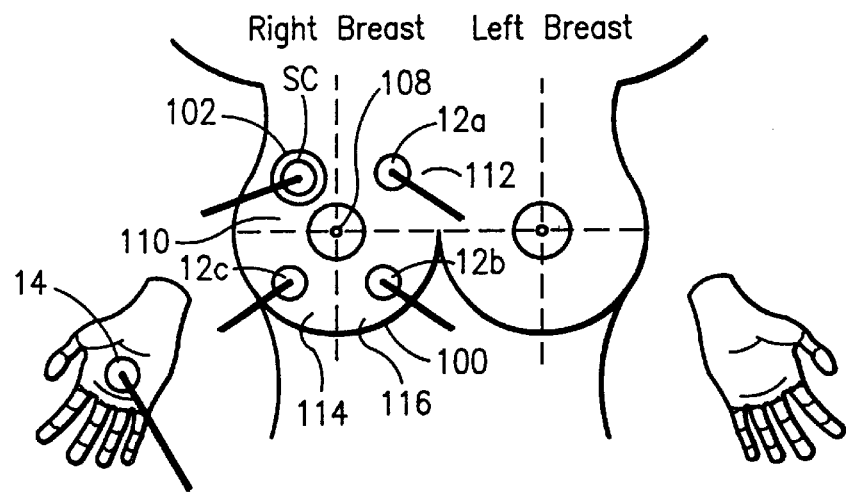
FIG. 5 is a diagram showing a second sensor placement method of the present invention.
Figures 6, 7:
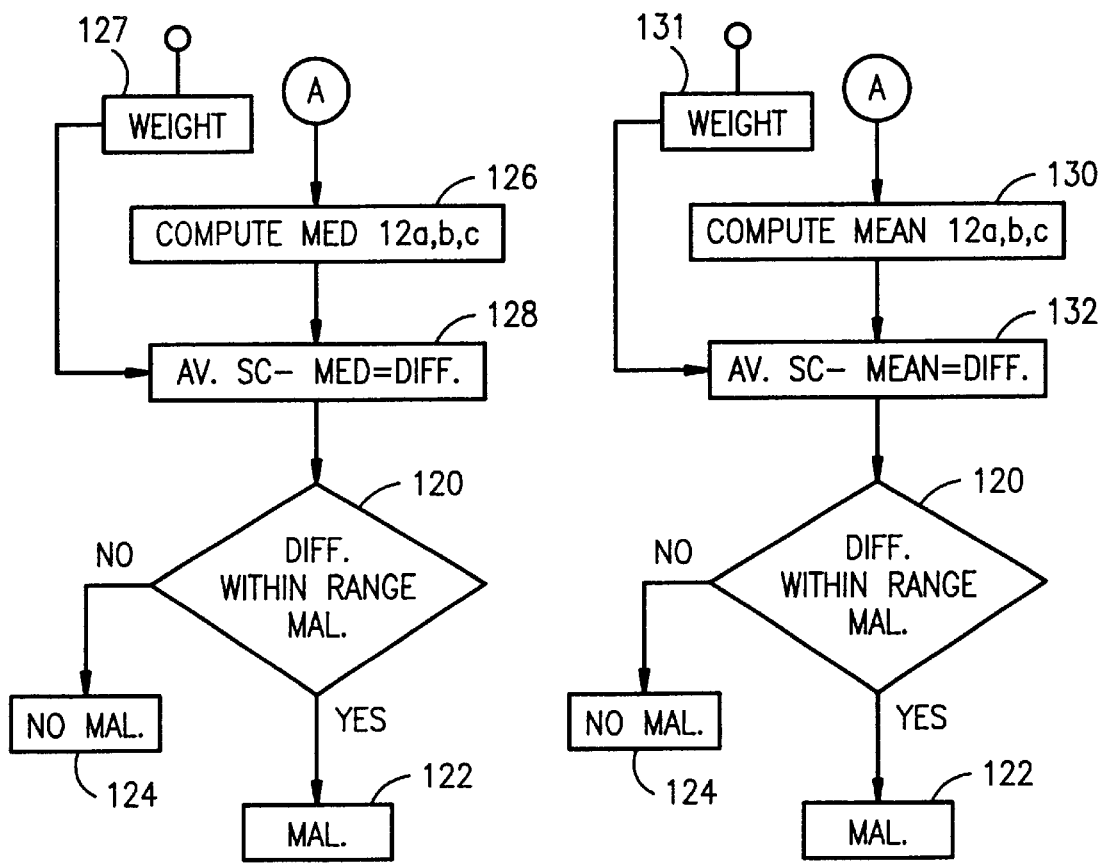
FIG. 6 is a flow diagram illustrating the operation of the apparatus of FIG. 1 with the sensor placement of FIG. 5.
FIG. 7 is a flow diagram modification of the flow diagram of FIG. 6.

Referring to FIGS. 5 and 6, an enhanced noise rejection arrangement and operation for the apparatus 10 is illustrated. Here, in addition to the lesion test sensor SC in quadrant 110 of the symptomatic breast 100, non-lesion test sensors 12a, 12b, and 12c are located in each of the non-lesion quadrants 112, 114 and 116 of the symptomatic breast. The processor 70 during a test period causes the same number of plural measurements to be taken by the sensors SC, 12a, 12b and 12c and an average is obtained at 98 for each sensor as previously described. Then, as illustrated by FIG. 6, the processor 70 calculates a median value of the average values for the sensors 12a, 12b and 12c at 126 and at 128 subtracts this median value from the average value from the sensor SC to obtain a differential value. Again, the values used to obtain the differential value may be weighted at 127 in a manner to be described. This differential value is then compared at 120 to the predetermined reference value previously described to obtain a prediction of malignancy at 122 or of non-malignancy at 124.

Alternatively, as illustrated by FIG. 7, rather than calculate the median value of the average values for the sensors 12a, 12b and 12c, the processor 70 may be programmed to calculate the mean value of these averages at 130. This mean value is then subtracted at 132 from the average value from the sensor SC to obtain a differential value which is then compared to a reference at 120 as previously described. Weighting may be applied at 131 for the calculation of the differential value.

Turning now to FIGS. 8 and 9, a greatly enhanced noise rejection arrangement and operation for the apparatus 10 is shown. Here, as in FIG. 5, the non-lesion test sensors 12a, 12b and 12c are positioned in the non-lesion quadrants of the symptomatic breast 100. In this case, however, the asymptomatic breast 134 is divided into four quadrants 136, 138, 140 and 142 in the same manner that was done for the symptomatic breast, so that the quadrants in the asymptomatic breast match those in the symptomatic breast. Then sensors 12d, 12e, 12f and 12g are positioned in each of the quadrants 136, 138, 140 and 142 respectively to match the positions of the sensors SC, 12a, 12b and 12c respectively on the symptomatic breast. During a test period, the processor 70, in addition to causing a plurality of measurements equal in number to be taken by the sensors SC, 12a, 12b and 12c, also causes an equal number of measurements using the reference sensor 14a to be taken by the sensors 12d, 12e, 12f and 12g. Then, as previously described in connection with FIG. 2, the processor obtains an average for each sensor in the symptomatic and the asymptomatic breast.

Referring now to FIG. 9, at the end of the test period, the processor 70 samples at 144 the highest average value and the lowest average value from the sensors on the asymptomatic breast and then at 146 subtracts the lowest average from the highest average to obtain a maximum voltage differential value (MVD) for the asymptomatic breast. Also, as described in connection with FIG. 6, the processor computes the median value of the averages from the sensors 12a, 12b and 12c on the symptomatic breast at 148 and at 150 subtracts this median value from the average value for the sensor SC to obtain a basic differential value, and then, the processor adds the maximum differential voltage value from the asymptomatic breast to the basic differential value to obtain a final differential value (FDIFF). The values used to obtain the final differential may be weighted at 152 in a manner to be described.

At 154, the final differential value is, as previously described relative to FIGS. 4, 6 and 7, compared with a predetermined reference and if it doesn't fall within a determined range, an indication of no malignancy is given at 156. If on the other hand the final differential value falls within the determined range, malignancy is indicated at 158.

Figure 10:
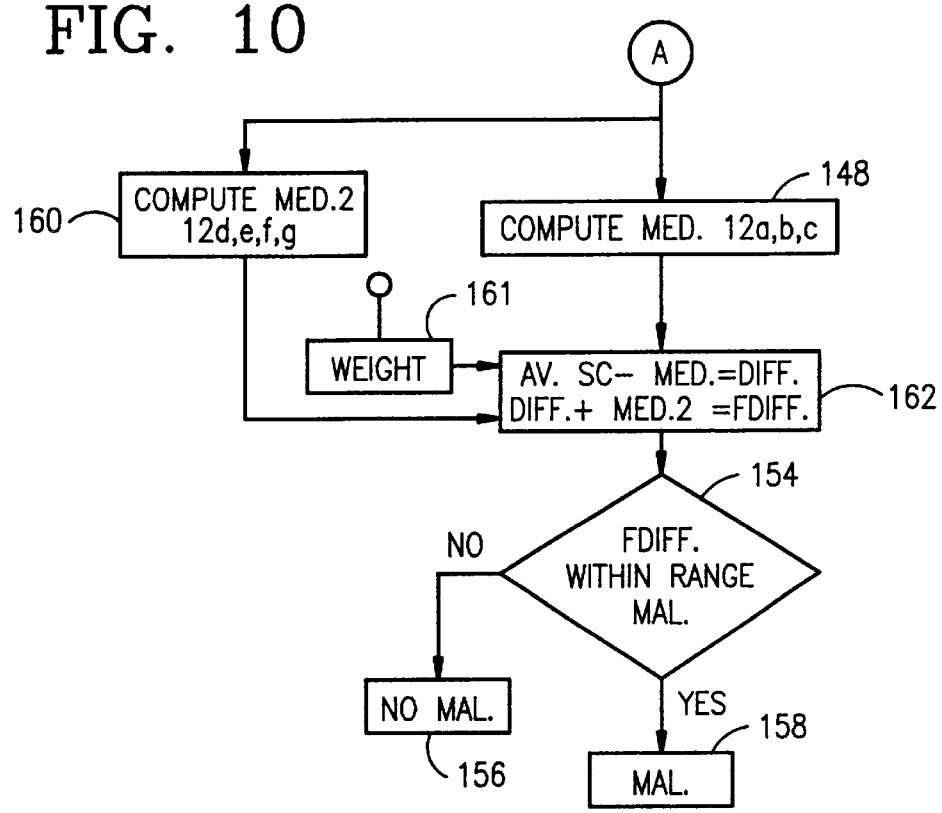
FIG. 10 is a flow diagram illustrating a second mode of operation of the apparatus of FIG. 1 with the sensor placement of FIG. 8.

Referring to FIG. 10, a second form of the final differential can be calculated by the processor 70 by computing the median value (MED 2) of the averages for each sensor channel for the sensors 12d, 12e, 12f and 12g at 160. This median value for the asymptomatic breast is then added to the differential value at 162 which has been obtained by subtracting from the SC value the median value of the averages for the sensors 12a, 12b and 12c computed at 148. These values may be weighted at 161 to obtain a final differential value. Now the processor operates in the same manner described with respect to FIG. 9 to obtain an indication of malignancy or non-malignancy.

Figure 11:
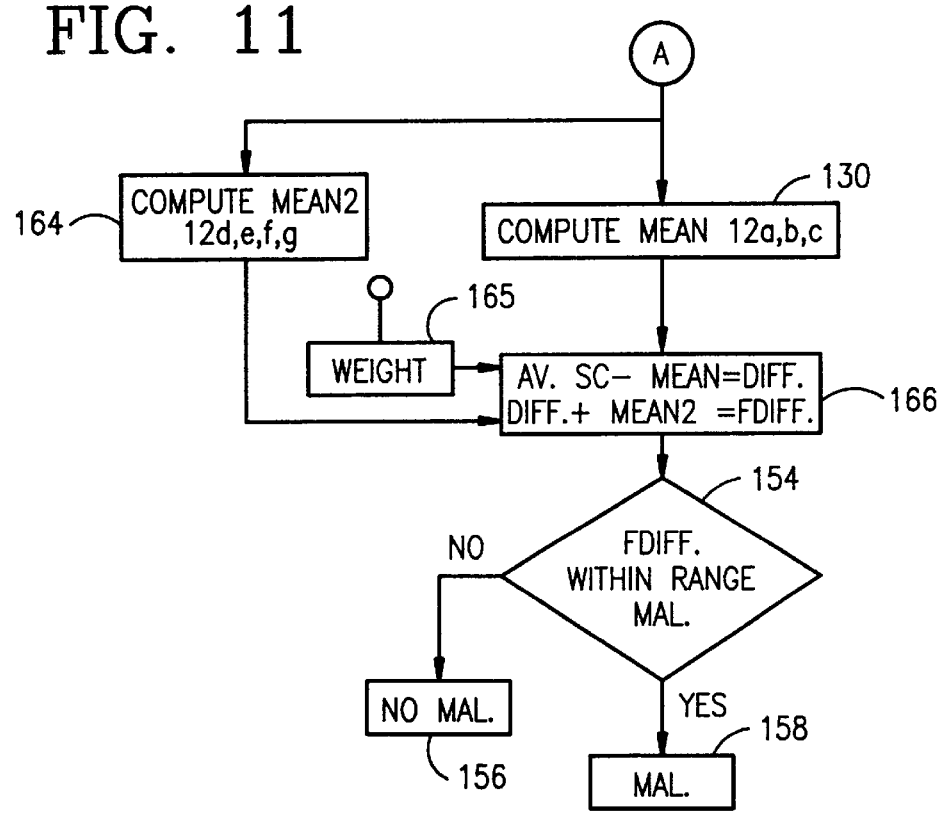
FIG. 11 is a flow diagram illustrating a third mode of operation of the apparatus of FIG. 1 with the sensor placement of FIG. 8.
Figure 12:
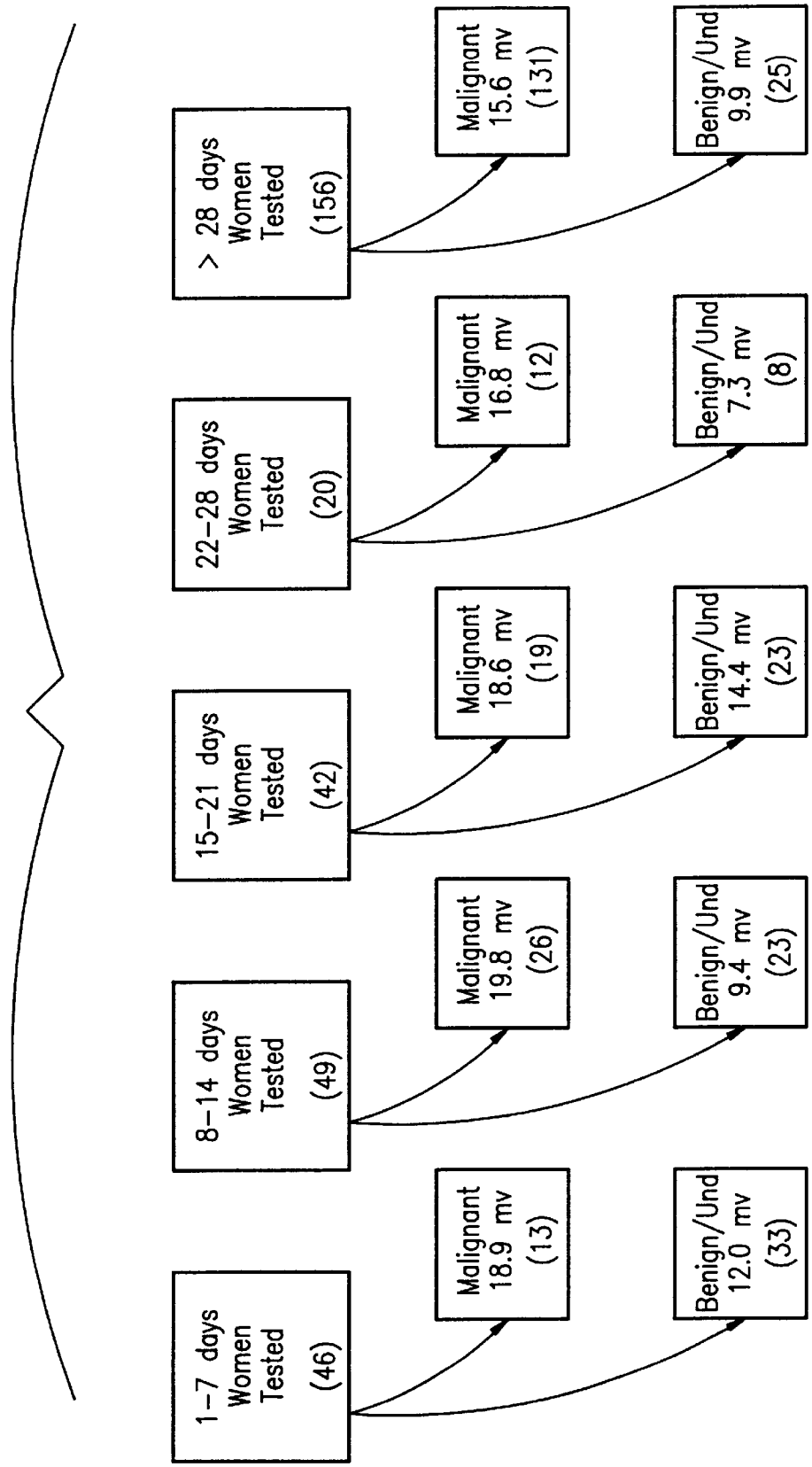
FIG. 12 is a chart showing average electropotential breast measurements taken from a plurality of women during the menstrual cycle.

As illustrated in FIG. 11, the processor 70 may operate at 130 in the manner described in connection with FIG. 7 to compute a mean value from the averages for sensors 12a, 12b and 12c and then at 166 to obtain a differential value for the symptomatic breast by subtracting this mean value from the average value from sensor SC. Here, however, the processor obtains a mean value (MEAN 2) for the asymptomatic breast at 164 which is the mean of the average values from the sensors 12d, 12e, 12f and 12g. Then this asymptomatic breast mean value is added to the differential value at 166 to obtain the final differential value which is then processed at 154 in the manner described with respect to FIG. 9 to obtain an indication at 156 or 158. The values used to obtain the final differential value may first be weighted at 165.

In FIG. 8, only four sensors have been shown on each breast, but fewer or more sensors could be used so long as the sensors on the asymptomatic breast are placed at sites which mirror image the sensor placement sites on the symptomatic breast. Also, preferably the same number of sensors are used in each non-lesion quadrant of the symptomatic breast.

Turning now to the weighting factors which may be used with the values arithmetically combined to determine the differential value in FIGS. 4, 6 and 7 and the final differential value in FIGS. 9, 10, and 11, these weighting factors may be stored in the memories for the processor 70, may be computed by the processor in accordance with data provided at the data input 75 relative to patient physiological conditions, or preferably are a combination of both. Considering first the non-physiological weighting factors, these are determined on the basis of training data obtained using the apparatus 10 on a test population of women within the desired age range with palpable lesions of a known type to establish the predictive value of the variables used to determine the differential or final differential value. For example, to obtain the differential values in FIGS. 4, 6 and 7 and the final differential values in FIGS. 9, 10 and 11, the average value of the electropotentials from SC is weighted by a value which is higher than the value used to weight the average of the electropotentials for sensor 12a in FIG. 4, the median of the electropotentials from sensors 12a, b and c in FIGS. 5, 9 and 10, and the mean of the electropotentials from sensors 12a, b and c in FIGS. 7 and 11. As an example, in FIGS. 5, 9 and 10, the weighting of the average SC and the median at 128, 150, and 162 could be in accordance with the following specific equation:

$$0.0623SC - 0.0380MED = DIFF$$

When values from the asymptomatic breast are added to the equation, these values are weighted by a value which is less than the weighted value applied to SC, MED or MEAN. For example, in FIG. 9 at 150, the equation could be:

$$0.0623SC - 0.0380MED = DIFF + 0.0214MVD = FDIFF$$

Finally, a constant can be added to each of the calculations for the differential values in FIGS. 4, 6 and 7 and the final differential values in FIG. 9, 10 and 11. This constant has two components; a first due to the mean of the variables in the training data and a second due to the prevalence in the data which affects the output scale. By applying this constant, the equation for FIGS. 5, 9 and 10 at 128, 150 and 162 could be:

$$-4.6689 + 0.0623SC - 0.0380MED = DIFF$$

Thus in FIG. 9 at 150, the complete equation could be:

$$-4.6689 + 0.0623SC - 0.0380MED = DIFF + 0.0214MVD = FDIFF$$

In addition to weighting on the basis of training data, each of the arithmetic calculations in FIGS. 4, 6, 7, 9, 10 and 11 can be weighted in accordance with physiological factors present in the patient which affect the outcome of the calculation. These physiological factors include patient age, menses, i.e. the time in the patient's menstrual cycle, the effects of hormonal agents and the time of day when the test is taken. Weighting factors for one, a plurality or all of these physiological factors can be applied to the arithmetic calculation which results is the differential or final differential value which is evaluated.

Because of the increasing prevalence of cancer with age, a statistically significant improvement in discrimination between malignancy and non-malignancy is found when the calculation is weighted for age. Thus a weighting factor which varies with age can be added to the value of SC in FIGS. 4, 6, 7, 9, 10 and 11. The age of the patient is entered at the data input 75, and the processor 70 provides a weighting factor from a stored factor index based upon age. This age weighting factor is added to SC as follows:

FIG. 4: Age factor+SC−AV 12$a$=DIFF

FIGS. 6, 9, 10: Age factor+SC−MED=DIFF

FIGS. 7, 11: Age factor+SC−MEAN=DIFF

Obviously the age weighting factor or the other physiological weighting factors can be combined with the weighting factors previously described. Thus, when age is taken into account, the complete equation for FIG. 9 could be:

$$-4.6689 + \text{Age factor} + 0.0623 SC - 0.0380 MED = DIFF + 0.0214 MED = FDIFF$$

It is a well known fact that various changes occur in the human female body during the phases of the menstrual cycle. These changes result from changes in levels of certain hormones, and a spectrum of changes occur in the female breasts which affect the measurements made by the device 10. Interestingly, the measurements of malignant lesions have been found to remain relatively stable throughout the menstrual cycle, but benign lesions measurements vary significantly as illustrated by the chart in FIG. 12 which shows the average measurements for a plurality of women taken at various times in the menstrual cycle. This directly affects the separation of potentials corresponding to benign and malignant tumors. Consequently, a test result which indicates malignancy may be accurate regardless of menses, but when the result is indicative of a benign tumor the result may not be accurate due to the effect of menses. When the processor 70 senses that the results have occurred during a period in the menstrual cycle where benign results have an unacceptably high probability of being false, the processor can cause the display to show a recommendation to delay the test until a specified date along with a range of dates during which a retest may be performed. Alternatively, a retest could be performed immediately by first providing an input to the processor to have the processor add a weight factor to SC or another electropotential variable in the equation. Also it is possible to have the processor add a menstrual variable to the entire equation which, like the weight factor, is determined by the period in the menstrual cycle to compensate for the variation in benign measurement indications. The addition of this factor during a remeasurement would determine whether or not the differential was truly in the benign range.

Figure 13:
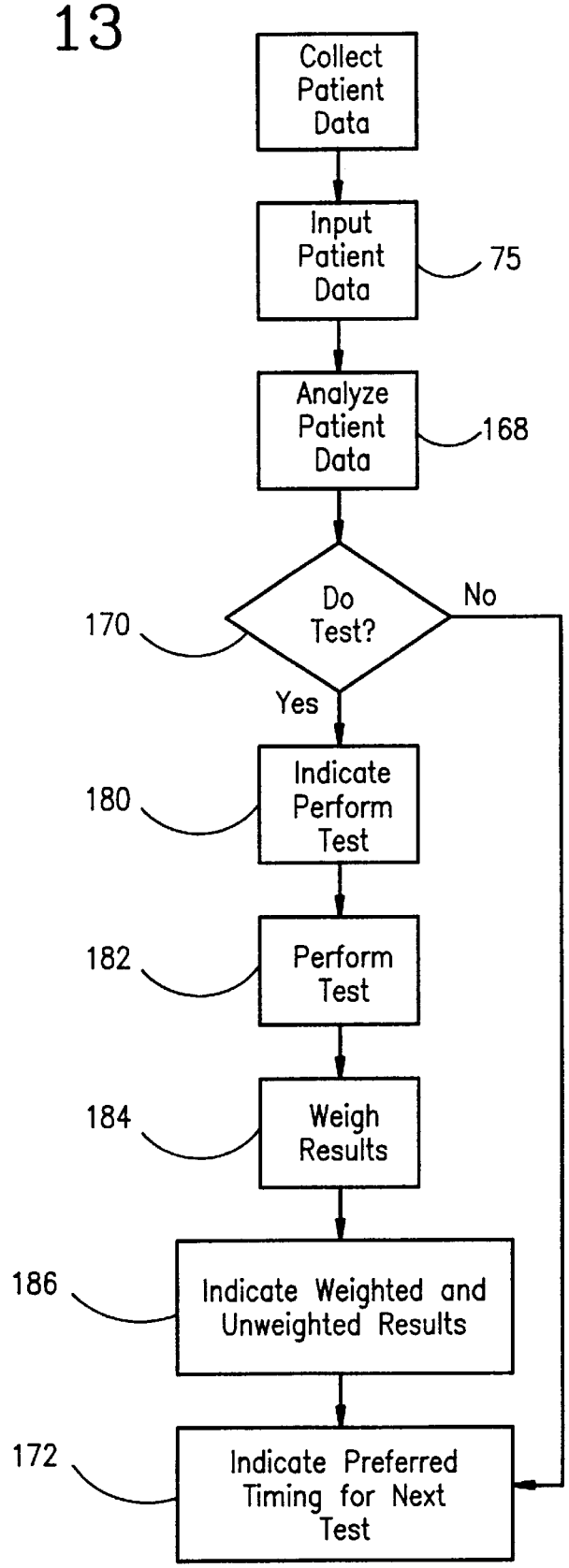
FIG. 13 is a flow diagram illustrating the operation of the apparatus of FIG. 1 to weight measurement results for menses.

Also during menses, when the results of previously taken adjunctive cancer tests are input at 75 to the processor 70, these tests relative to the real time test taken by the device 10 can be weighted in accordance with menses. With reference to FIG. 13, relevant data input at 75 can include patient age, family and personal medical history, medication or hormone usage, results and dates of recent adjunctive cancer tests (such as mammography or ultrasound), results and dates of recent hormone measurement tests (such as sputum or urine sample analysis), and date of onset of last menstrual period and time of day. Using all related menstrual data, including hormone usage and test results, the system processor 70 performs an analysis 168 and then decides at 170 if a cancer test should be performed by the system 10 at this time. If the analysis indicates that the results may have an unacceptably high probability of being false, the indicator 76 is instructed to display a recommendation 172, such as delaying the test until a specified date, along with a range of dates during which the test may be performed. If the analysis indicates that the results may have a reliable outcome, the indicator is instructed to display a recommendation to proceed with the test 180. The real time test is then performed at 182, collecting and processing the potentials from sensors 12. The processor 70, according to its programmed algorithm, combines at 184 the results of the analysis 168 with that of the real time test 182. Finally, the results are displayed at 186 via the indicator 76 in the form of the real time test results of the real time test 182 and the patient data analysis 168.

The combined results 186 may take several forms. As an example, it may be a weighted combination of the results of the real time test and the recent adjunctive tests. The weights are determined by the dates of menses and/or hormonal levels. The rationale for this is that the real time test is more reliable under certain conditions relating to the hormonal levels and the adjunctive tests are more reliable under certain other conditions. As a simple example, during the second week of the menstrual cycle the real time test and the adjunctive test are equally reliable. Thus, they are weighted equally in the final results. On the other hand, during the fourth week of the menstrual cycle, the adjunctive test is only half as reliable as the real time test and it is given a 25% weighting vs. a 75% weighting for the adjunctive test. This may be reflected in a statistically derived sensitivity and specificity index.

In addition to the menstrual cycle, another factor which appears to affect DC biopotential breast measurements is the time of day during which a measurement is taken. Physiological changes which apparently occur in females as a day progresses cause significant changes in the data obtained from biopotential breast measurements taken with the device 10, particularly when a palpable lesion is present. For women measured at the same time in the menstrual cycle or for measurements taken in post menopausal women, there have been found to be substantial differences in the results of measurements taken from the same women early in a day and later in the day. Using 2:00 pm as a hypothetical boundary time, tests have shown that DC biopotential breast measurements taken in the afternoon from an electrode placed over a palpable breast lesion may be 8 to 10 mV higher than the same measurements taken in the morning. Consequently, the time of day entered at data input 75 for the apparatus 10 can be a significant factor for measurements taken by one or more of the sensors 12. The time of day can be used by the processor 70 to apply a weighting factor to the measurements taken in the manner previously described.

The effects of estrogen increase the electropotential difference between depolarized and polarized tissue more when malignant tissue is present than when a lesion is benign. This in part is responsible for the effect menses has on DC biopotential breast measurements. The effects of estrogen can be turned to practical use by applying estrogen to a symptomatic breast 100 before measurements are taken. This can be accomplished by adding estrogen to the ion conducting gel or cream 19 in the electrodes applied to the symptomatic breast, or estrogen can be applied directly to the symptomatic breast before application of the electrodes.

In applying electrodes to the symptomatic breast, it has been found to be beneficial to maintain a pressure on electrode SC which forces this electrode downwardly against the breast over the lesion. The application of this downward pressure to only the electrode SC can be achieved by the design of a harness or brassiere 188 which mounts the electrodes for the symptomatic breast. The electrode SC can be mounted to project outwardly further from the mounting unit 188 than the remaining test electrodes as shown by the broken lines in FIG. 14. Resilient cushioning 190 between the electrode SC and the mounting unit 188 will force the electrode SC against the symptomatic breast with a greater force than that applied to adjacent test electrodes on the symptomatic breast.

Figure 15:
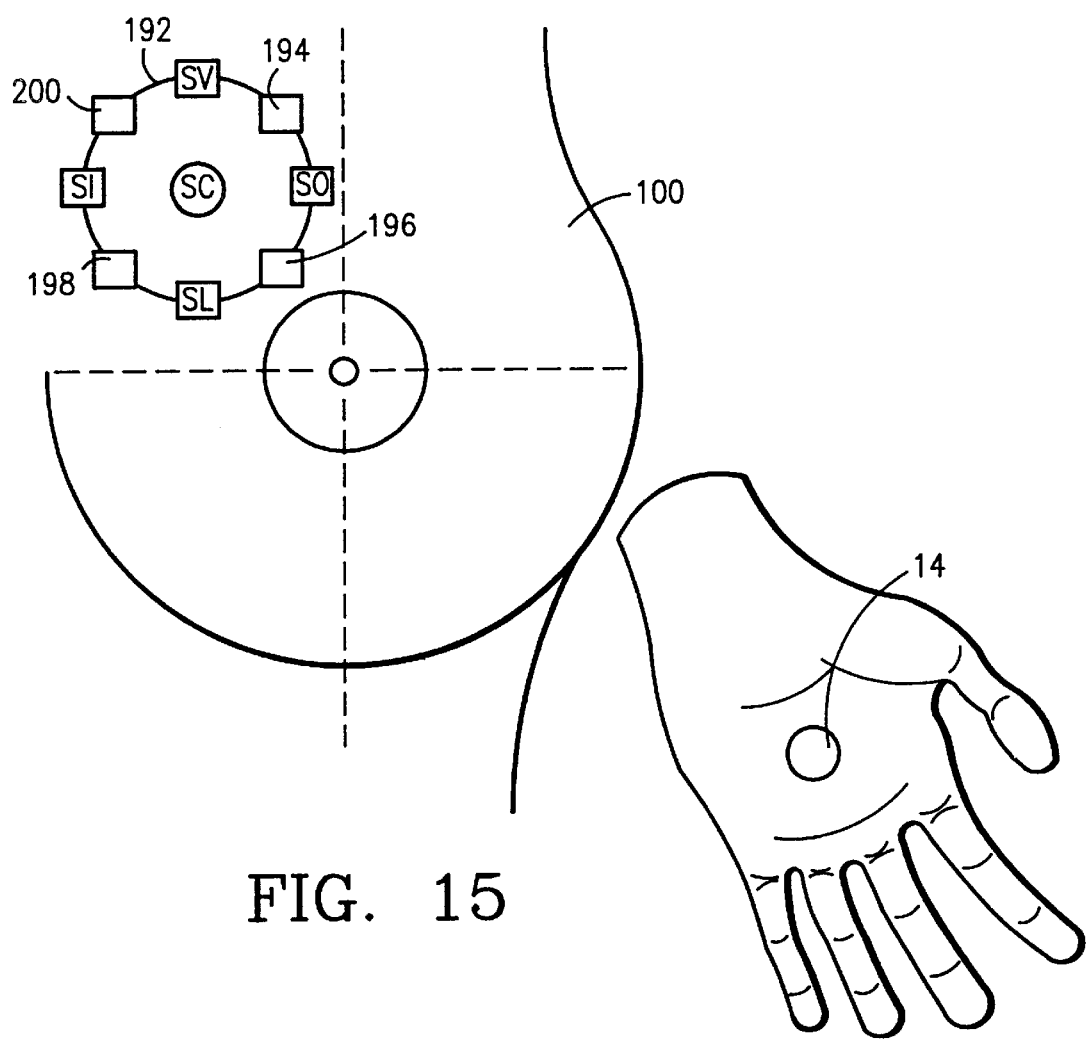
FIG. 15 is a diagrammatic view of sensor placement for gradient approximation.

It has been observed that the gradient around a tested lesion is relatively large among malignant cases. As shown in FIG. 15, this gradient may be approximated by arranging electrodes in one or more concentric circles on the symptomatic breast with the electrode SC at the center of the circles over the lesion. At least four electrodes SU, SI, SO and SL are spaced on a concentric circle 192 around the central electrode SC. Using measurements from these five electrodes SC, SU, SI, SO and SL relative to a reference sensor 14, the gradient may be approximated.

$$\text{Curve\_s} = SC - \tfrac{1}{4}(SU+SL+SI+SO)$$

If SC through error has not been placed sufficiently near the site of the maximum depolarization, there could be diminished separation between malignant and benign measurement results. When this occurs, the above equation fitted to the electropotential response surface of the symptomatic breast can be used to estimate the location of maximum response for SC. The five sensors SC, SU, SL, SI and SO in the quadrant of the lesion can be seen in the language of factual design as a $2^2$ with a center point. With this design, the curvature, main effects and interaction between two orthogonal, directional axes A and B can be checked. If SC is properly placed at the location of maximum response, the curvature contrast derived from the above equation should be statistically greater or equal to zero. If this curvature contrast is statistically less than zero, the sensor SC may have been incorrectly placed.

The raw electrical measurements provided by SC, SU, SL, SI and SO may be in a wide range, and to normalize the gradient, curve_s is divided by the standard deviation (std) of SU, SL, SI and SO. The variable to be evaluated is:

$$\text{Curve\_sd} = \text{Curve\_s}/\text{std}(SU+SL+SI+SO)$$

To provide more accurate measurements based upon those from SC and surrounding sensors, the number of sensors concentrically spaced around the lesion can be increased beyond the four sensors described as indicated at 194, 196, 198 and 200 in FIG. 15.

Figure 16:
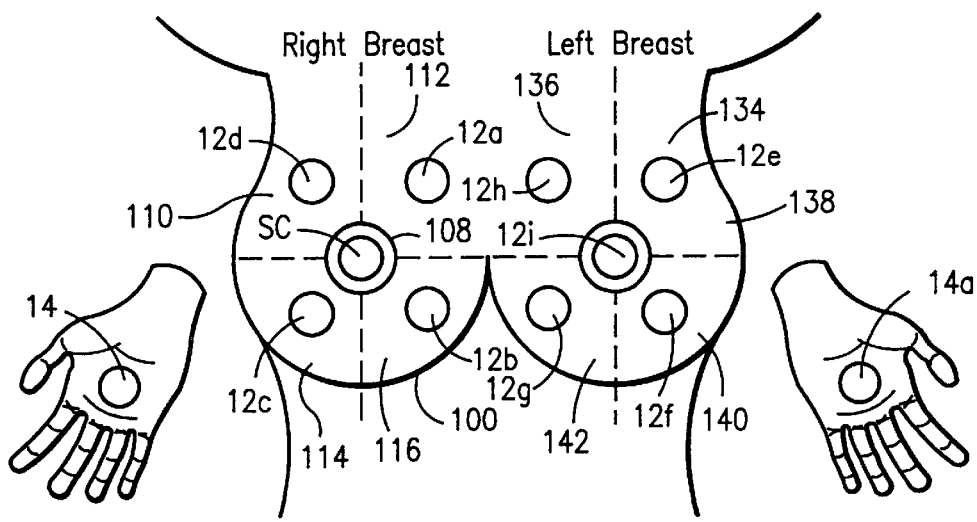
FIG. 16 is a diagram showing a sensor placement for breast measurements using a nipple sensor.

In some cases, a lesion is not readily discernable and the sensor SC cannot accurately be located over the lesion. Since all conduits in the breast lead to the nipple, the sensor SC can be located over the nipple 108 on a suspected symptomatic breast 100 as shown in FIG. 16. Then, preferably at least one non-lesion test sensor 12a, 12b, 12c and 12d is placed in each of the four quadrants of the symptomatic breast as illustrated in FIG. 16. However, if non-lesion test sensors are used in only one quadrant, the process described in connection with FIGS. 3 and 4 will be performed.

When non-lesion test sensors are located in all four quadrants of the symptomatic breast, then a process similar to that described in connection with FIGS. 5 and 6 or 5 and 7 is used except now average values for four sensors 12a, 12b, 12c and 12d are used to calculate either a median or mean value to be subtracted from the average value for SC rather than average values for only three sensors as previously described.

Also, when a nipple sensor SC and non-lesion test sensors are used on the symptomatic breast, enhanced noise rejection can be achieved by using mirror image sensors as shown in FIG. 16 on the asymptomatic breast 134. Again, these sensors 2e, 12f, 12g, 12h and 12i provide five averaged outputs instead of the four described in connection with FIGS. 8–11, but these five average outputs are used to provide a maximum voltage differential value (MCV), a median value, or a mean value for the asymptomatic breast as previously described. These asymptomatic breast values are combined with the symptomatic breast values as described relative to FIGS. 8–11.

Figure 17:
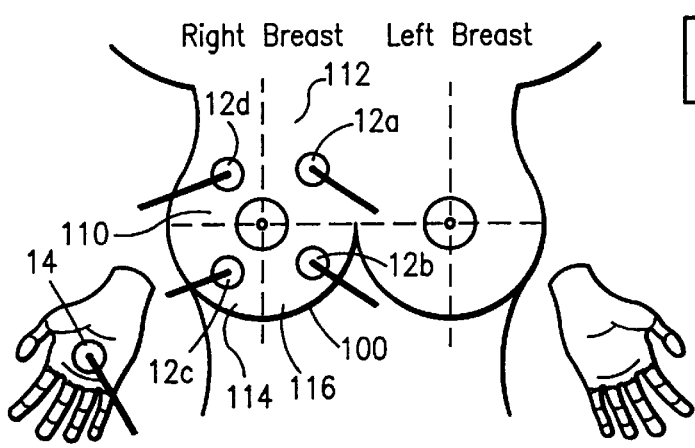
FIG. 17 is a diagram showing sensor placement for breast screening.
Figure 18:
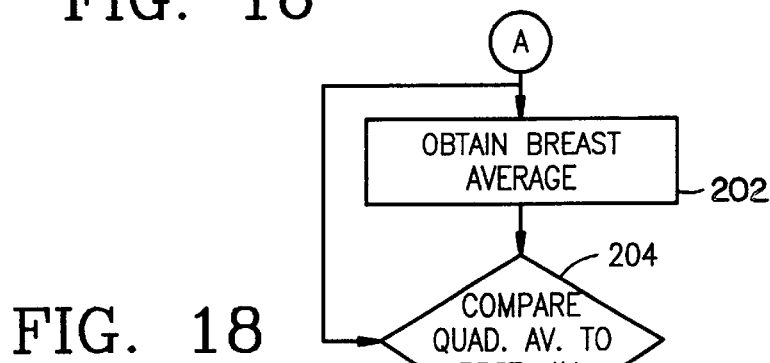
FIG. 18 is a flow diagram illustrating a screening mode of operation for the apparatus of FIG. 1 with the sensor placement of FIG. 17.

The apparatus 10 may be used to screen a breast 100 as illustrated in FIGS. 17 and 18. Here, at least one sensor 12a, 12b, 12c, 12d is placed in each quadrant of a breast to be screened and during a screening period, the apparatus operates in accordance with the process described in connection with FIG. 2 to obtain an average potential value for each breast quadrant. The processor 70 then compares the average potential values for each breast quadrant, and if one breast quadrant value varies from the others by more than a predetermined amount, the processor identifies that breast quadrant as a potential lesion containing quadrant. As shown in FIG. 18, the processor may operate to average the breast quadrant values to obtain a breast average value at 202 and to then compare each individual breast quadrant value with the breast average value at 204. If a breast quadrant value varies from a breast average value by more than a predetermined amount x at 206, the processor 70 identifies that breast quadrant as a potential lesion containing quadrant at 208. Once this occurs, the processor may then institute a test period using the sensor in the lesion quadrant as SC and the remaining one or more quadrant sensors as described in connection with FIGS. 3–11, or a nipple sensor SC may be added as described in connection with FIG. 16. If the quadrant average value does not vary by more than X at 206, no lesion is indicated at 210.

We claim:

1. An apparatus for sensing and processing electropotentials from the symptomatic breast of a human female subject which includes a lesion containing quadrant and a plurality of non-lesion containing quadrants comprising:

at least one DC biopotential reference sensor for contacting the female subject at a reference location, and each at least one DC biopotential test sensors for contacting the symptomatic breast operating with a reference sensor during a test period to detect electropotentials and to provide output test potentials, one of said test sensors forming a lesion test sensor for contact with a skin surface of the symptomatic breast over the lesion in the lesion containing quadrant and another test sensor forming a first non-lesion test sensor for contact with a skin surface of the symptomatic breast in a first non-lesion quadrant, separate from said lesion quadrant, a third of said test sensors forming a second non-lesion test sensor for contact with a skin surface of the symptomatic breast in a second non-lesion quadrant separate from said lesion and first non-lesion quadrants and a fourth of said test sensors forming a third non-lesion test sensor for contact with a skin surface of the symptomatic breast in a third non-lesion quadrant separate from said lesion and first and second non-lesion quadrants, a signal processing section being connected to separately receive the output test potentials provided by said reference sensor and lesion test sensor and said reference sensor and first, second and third non-lesion test sensors, said processing section including a processor for obtaining a first variable from said output test potentials provided by said reference sensor and lesion test sensor and a second variable by arithmetically combining all of said output test potentials provided by said reference sensor and said first, second and third non-lesion test sensors, the processor operating to subtract the second variable from the first variable to obtain a first differential value.

2. The apparatus of claim 1 wherein said processor operates to compare said first differential value to a reference value to determine a relationship therebetween.

3. The apparatus of claim 1 wherein said processor obtains a median value from the output test potentials provided by said reference sensor with said first, second and third non-lesion test sensors as said second variable.

4. The apparatus of claim 1 wherein said processor operates during a test period to sample and receive a first plurality of output test potentials from said reference sensor and said lesion test sensor and to average said first plurality of output test potentials to obtain a first average value as said first variable, and to sample and receive a second plurality of output test potentials from said reference sensor and said first non-lesion test sensor, a third plurality of output test potentials from said reference sensor and said second non-lesion test sensor, and a fourth plurality of output test potentials from said reference sensor and said third non-lesion test sensor, said processor operating to obtain a second average value from said second plurality of output test potentials, a third average value from said third plurality of output test potentials and a fourth average value from said fourth plurality of output test potentials and to use said second, third and fourth average values to obtain said second variable.

5. The apparatus of claim 4 wherein said processor operates to sample and receive during a test period the same number of output test potentials from said reference sensor and lesion test sensor and said reference sensor and first, second and third non-lesion test sensors.

6. The apparatus of claim 5 wherein said processor operates to obtain a median value of said second, third and fourth average values as said second variable.

7. The apparatus of claim 6 wherein said processor operates to compare said first differential value to a reference value to determine a relationship therebetween.

8. The apparatus of claim 5 wherein said processing section includes a storage unit for storing a plurality of weighting factor values including a first arithmetic weighting factor value and a second arithmetic weighting factor value, said processor operating to retrieve and apply said first weighting factor value to said first average value and said second weighting factor value to said second variable before subtracting said second variable from said first variable.

9. The apparatus of claim 8 wherein said first stored arithmetic weighting factor is greater than said second stored weighting factor value.

10. The apparatus of claim 5 wherein said processing section includes a storage unit which stores menstrual cycle weighting factor values which vary in value in accordance with the period in the menstrual cycle of a human female subject and an input unit for inputting the period in the menstrual cycle of a human female subject under test, said processor operating in response to a menstrual cycle period input from said input unit to select a stored menstrual cycle weighting factor value and to apply said menstrual cycle weighting factor value to said first average value before subtracting said second variable from said first variable.

11. The apparatus of claim 5 wherein said processing section includes a storage unit which stores age weighting factor values which vary in value in accordance with the age of a human female subject and an input unit for inputting the age of a human female subject under test, said processor operating in response to an age input from said input unit to select a stored age weighting factor value and to apply said age weighting factor value to said first average value before subtracting said second variable from said first variable.

12. The apparatus of claim 5 wherein said processing section includes a storage unit which stores time of day weighting factor values which vary in value in accordance with the time of day during which a test period occurs, and an input unit for inputting the time of day when the test period is to occur, said processor operating in response to a time of day input from said input unit to select a stored time of day weighting factor value and to apply said time of day weighting factor value to said first average value before subtracting said second variable from said first variable.

13. The apparatus of claim 1 which includes at least four DC biopotential test sensors for contacting an asymptomatic breast of a human female subject and each operating with a reference sensor during a test period to detect electropotentials and provide output test potentials, the four DC biopotential test sensors for contacting the asymptomatic breast including a fifth test sensor for contact with the skin surface of the asymptomatic breast in a location corresponding to the location on the symptomatic breast of the lesion test sensor and a sixth, seventh and eighth test sensor for contact with the skin surface of the asymptomatic breast in locations corresponding to the location of on said symptomatic breast of said first, second and third non-lesion test sensors respectively, said signal processing section being connected to separately receive the output test potentials provided by said reference sensor and said fifth, sixth, seventh and eighth test sensors, said processor operating to provide an asymptomatic breast value from the output test potentials provided by said reference sensor and said fifth, sixth, seventh and eighth test sensors and to add said asymptomatic breast value to said first differential value to obtain a final value.

14. The apparatus of claim 13 wherein said processor operates to compare said final value to a reference value to determine a relationship therebetween.

15. The apparatus of claim 13 wherein said processor operates to compare the output test potentials provided by said reference sensor and said fifth, sixth, seventh and eighth test sensors respectively to identify a highest and lowest output test potential and to subtract said lowest output test potential from said highest output test potential to obtain a second differential value as said asymptomatic breast value.

16. The apparatus of claim 13 wherein said processor operates to obtain a median value from the output test potentials provided by said reference sensor and said fifth, sixth, seventh and eighth test sensors respectively as said asymptomatic breast value.

17. The apparatus of claim 13 wherein said processor operates to obtain a mean value from the output test potentials provided by said reference sensor with said first, second and third non-lesion test sensors as said second variable.

18. The apparatus of claim 17 wherein said processor operates to obtain a mean value from the output test potentials provided by said reference sensor and said fifth, sixth, seventh and eighth test sensors respectively, as said asymptomatic breast value.

19. The apparatus of claim 5 which includes at least four DC biopotential test sensors for contacting an asymptomatic breast of a human female subject and each operating with a reference sensor during a test period to detect electropotentials and provide output test potentials, the four DC biopotential test sensors for contacting the asymptomatic breast including a fifth test sensor for contact with the skin surface of the asymptomatic breast in a location corresponding to the location on the symptomatic breast of the lesion test sensor and a sixth, seventh and eighth test sensor for contact with the skin surface of the asymptomatic breast in locations corresponding to the location on said symptomatic breast of said first, second and third non-lesion test sensors respectively, said signal processing section being connected to separately receive the output test potentials provided by said reference sensor and said fifth, sixth, seventh and eighth test sensors, said processor operating during a test period to sample and receive a plurality of output test potentials from said reference sensor and each of said fifth, sixth, seventh and eighth test sensors respectively and to average the plurality of output test potentials from said reference sensor and said fifth test sensor to obtain a fifth average value, from said reference sensor and said sixth test sensor to obtain a sixth average value, from said reference sensor and said seventh test sensor to obtain a seventh average value and from said reference sensor and said test sensor to obtain an eighth average value, said processor operating to provide an asymptomatic breast value from said fifth, sixth, seventh and eighth average values and to add said asymptomatic breast value to said first differential value to obtain a final value.

20. The apparatus of clam 19 wherein said processor operates to sample and receive during a test period the same number of output test potentials from a reference test sensor and said fifth, sixth, seventh and eighth test sensors respectively as said processor samples and receives from a reference sensor and said lesion test sensor, and first, second and third non-lesion test sensors respectively.

21. The apparatus of claim 20 wherein said processor operates to obtain a median value of said second, third and fourth average values as said second variable and operates to compare said fifth, sixth, seventh and eighth average values to identify a highest and lowest average value therefrom, said processor farther operating to subtract said lowest average value from said highest average value to obtain a second differential value as said asymptomatic breast value.

22. The apparatus of claim 21 wherein said processing section includes a storage unit which stores menstrual cycle weighting factor values which vary in value in accordance with the period in the menstrual cycle of a human female subject under test, and an input unit for inputting the period in the menstrual cycle of a human female subject to be tested, said processor operating in response to a menstrual cycle period input from said input unit to select a stored menstrual cycle weighting factor value and to apply said menstrual cycle weighting factor value to said first average value before subtracting said second variable from said first variable.

23. The apparatus of claim 21 wherein said processing section includes a storage unit which stores age weighting factor values which vary in value in accordance with the age of a human female subject under test, and an input unit for inputting the age of a human female subject, said processor operating in response to an age input from said input unit to select a stored age weighting factor value and to apply said age weighting factor value to said first average value before subtracting said second variable from said first variable.

24. The apparatus of claim 21 wherein said processing section includes a storage unit which stores time of day weighting factor values which vary in value in accordance with the time of day during which a test period occurs, and an input unit for inputting the time of day when the test period is to occur, said processor operating in response to a time of day input from said input unit to select a stored time of day weighting factor value and to apply said time of day weighting factor value to said first average value before subtracting said second variable from said first variable.

25. The apparatus of claim 23 wherein said processing section includes a storage unit, for storing a plurality of weighting factor values including a first arithmetic weighting factor value, a second arithmetic weighting factor value, and a third arithmetic weighting factor value, said processor operating to retrieve and apply said first weighting factor value to said first average value and said second weighting factor value to said second variable before subtracting said second variable from said first variable, and to apply said third weighting factor value to said asymptomatic breast value before adding said asymptomatic breast value to said first differential value.

26. The apparatus of claim 21 wherein said processing section includes a storage unit for storing a plurality of weighting factor values including a first arithmetic weighting factor value and a second arithmetic weighting factor value, said processor operating to retrieve and apply said first weighting factor value to said first average value and said second weighting factor value to said second variable before subtracting said second variable from said first variable.

27. The apparatus of claim 26 wherein said storage unit stores a third weighting factor value, said processor operating to apply said third weighting factor value to said asymptomatic breast value before adding said asymptomatic breast value to said first differential value.

28. The apparatus of claim 20 wherein said processor operates to obtain a first median value of said second, third and fourth average values as said second variable and a second median value of said fifth, sixth, seventh and eighth average values as said asymptomatic breast value.

29. The apparatus of claim 20 wherein said processor operates to obtain a first mean value of said second, third and fourth average values as said second variable and a second mean value of said fifth, sixth, seventh and eighth average values as said asymptomatic breast value.

30. A noninvasive method for sensing and processing biopotentials from a lesion containing first quadrant of a symptomatic breast of a human female subject using a plurality of spaced biopotential sensors which includes arranging at least one reference sensor in contact with a skin surface of said subject, arranging a plurality of test sensors with at least a first of said test sensors in contact with a skin surface of the subject in said first quadrant over said lesion and a least a second test sensor in contact with a skin surface of said subject in a second quadrant of the symptomatic breast which is outside said first quadrant, obtaining during a test period a first biopotential value using a reference sensor and said first test sensor to provide a first variable, obtaining during a test period a second biopotential value using a reference sensor and said second test sensor to provide a second variable, determining an arithmetic weighting factor in accordance with at least one physiological factor present in the human female subject during said test period, applying said arithmetic weighting factor to said first variable, and subtracting said second variable from said first variable to provide a first differential value.

31. The method of claim 30 which includes comparing said first differential value to a predetermined reference value to determine a relationship therebetween.

32. The method of claim 31 which includes positioning said second test sensor in a second quadrant positioned vertically relative to said first quadrant and using said second test sensor to obtain said second biopotential value.

33. The method of claim 31 which includes positioning said second test sensor in a second quadrant positioned horizontally relative to said first quadrant and using said second test sensor to obtain said second biopotential value.

34. The method of claim 30 which includes taking a plurality of biopotential measurements with said reference sensor and first test sensor during a test period to obtain a first plurality of measurement values.

35. The method of claim 34 which includes applying a first non-physiological arithmetic weighting factor to said first average value and applying a second non-physiological arithmetic weighting factor to said second average value before subtracting said second variable from said first variable.

36. The method of claim 35 wherein said first non-physiological weighting factor is greater than said second non-physiological weighting factor.

37. The method of claim 34 which includes determining an arithmetic weighting factor in accordance with the period in the menstrual cycle of the human female subject during which said test period occurs and applying said arithmetic weighting factor to said first average value before subtracting said second variable from said first variable.

38. The method of claim 34 which includes determining an arithmetic weighting factor in accordance with the age of the human female subject and applying said arithmetic weighting factor to said first average value before subtracting said second variable from said first variable.

39. The method of claim 34 which includes determining an arithmetic weighting factor in accordance with the time of day during which said test period occurs and applying said arithmetic weighting factor to said first average value.

40. The method of claim 30 which includes locating said reference sensor in spaced relationship to said symptomatic breast.

41. The method of claim 30 which includes locating said reference sensor at the sub-xyphoid area of the female subject.

42. The method of claim 30 which includes locating said reference sensor over the nipple of the symptomatic breast of the subject.

43. The method of claim 30 which includes applying estrogen to the skin surface of said symptomatic breast contacted by said first and second test sensors before obtaining said first and second biopotential values.

44. The method of claim 30 which includes applying pressure to the symptomatic breast with said first test sensor which is greater than the pressure applied to the symptomatic breast by the remaining test sensors.

45. A noninvasive method for sensing and processing biopotentials from a lesion containing first quadrant of a symptomatic breast of a human female subject using a plurality of spaced biopotential sensors which includes arranging at least one reference sensor in contact with a skin surface of said subject, arranging a plurality of test sensors with at least a first of said test sensors in contact with a skin surface of the subject over said lesion and at least a second test sensor in contact with a skin surface of said subject in a second quadrant of the symptomatic breast which is outside said first quadrant, at least a third test sensor in contact with a skin surface in a third quadrant of said quadrants of said symptomatic breast which is outside said first and second quadrants, and at least a fourth test sensor in contact with a skin surface in a fourth quadrant of the symptomatic breast which is outside said first, second and third quadrants, obtaining during a test period a first biopotential value using a reference sensor and said first test sensor to provide a first variable, using said reference sensor and second test sensor during the test period to obtain a second biopotential value, using said reference sensor and third test sensor during the test period to obtain a third biopotential value, using said reference sensor and fourth test sensor during the test period to obtain a fourth biopotential value, obtaining a median value of the sum of said second, third and fourth biopotential values as a second variable, and subtracting said second variable from said first variable to provide a first differential value.

46. The method of claim 45 which includes taking a plurality of biopotential measurements with said reference sensor and said second test sensor during said test period to obtain a second plurality of measurement values, taking a plurality of biopotential measurements with said reference sensor and said third test sensor during said test period to obtain a third plurality of measurement values, taking a plurality of biopotential measurements with said reference sensor and said fourth test sensor during said test period to obtain a fourth plurality of measurement values, averaging said second plurality of measurement values to obtain a second average value as said second biopotential value, averaging said third plurality of measurement values to obtain a third average value as said third biopotential value, and averaging said fourth plurality of measurement values to obtain a fourth average value as said fourth biopotential value.

47. The method of claim 46 which includes applying estrogen to the skin surface of said symptomatic breast contacted by said first, second, third and fourth test sensors before obtaining said first, second, third and fourth biopotential measurements.

48. The method of claim 46 which includes taking a plurality of biopotential measurements with said reference sensor and first test sensor during a test period to obtain a first plurality of measurement values, and averaging said first plurality of measurement values to obtain a first average value as said first variable.

49. The method of claim 48 which includes taking the same number of biopotential measurements with said first, second, third and fourth test sensors during a test period.

50. The method of claim 49 which includes comparing said first differential value to a predetermined reference value to determine a relationship therebetween.

51. The method of claim 45 which includes placing at least a fifth, sixth, seventh and eighth test sensor in contact with the skin surface of an asymptomatic breast in positions on the asymptomatic breast corresponding to the location of the first, second, third and fourth test sensors respectively on the symptomatic breast, using a reference sensor and said fifth, sixth, seventh and eighth test sensors during a test period to obtain fifth, sixth, seventh and eighth biopotential values respectively, comparing the respective fifth, sixth, seventh and eighth biopotential values so obtained to identify a high and a low level biopotential value, obtaining a second differential value indicative of the difference between said high and low level biopotential values, and adding said second differential value to said first differential value to obtain a final differential value.

52. The method of claim 51 which includes comparing said final differential value to a predetermined reference value to determine a relationship therebetween.

53. The method of claim 52 which includes determining an arithmetic weighting factor in accordance with the age of the human female subject and applying the arithmetic weighting factor to said first biopotential value.

54. The method of claim 52 which includes determining an arithmetic weighting factor in accordance with the period in the menstrual cycle of the human female subject and applying the arithmetic weighting factor to said first biopotential value.

55. The method of claim 52 which includes determining an arithmetic weighting factor in accordance with the time of day during which said test period occurs and applying said arithmetic weighting factor to said first biopotential value.

56. The method of claim 52 which includes applying a first arithmetic weighting factor to said first biopotential value and a second arithmetic weighting factor to said second biopotential value before subtracting said second variable from said first variable to provide said first differential value, and applying a third arithmetic weighting factor to said second differential value before adding said second differential value to said third differential value to obtain the final differential value.

57. The method of claim 56 wherein said first weighting factor is greater than said second weighting factor.

58. The method of claim 45 which includes placing at least a fifth, sixth, seventh and eighth test sensor in contact with the skin surface of an asymptomatic breast in positions on the asymptomatic breast corresponding to the location of the first, second, third and fourth test sensors respectively on the symptomatic breast, using a reference sensor and said fifth, sixth, seventh and eighth test sensors during a test period to obtain fifth, sixth, seventh and eighth biopotential values respectively, obtaining a second median value of said fifth, sixth, seventh and eighth biopotential values, and adding said second median value to said first differential value to obtain a final differential value.

59. The method of claim 58 which includes comparing said final differential value to a predetermined reference value to determine a relationship therebetween.

60. The method of claim 59 which includes determining an arithmetic weighting factor in accordance with the age of the human female subject and applying the arithmetic weighting factor to said first biopotential value.

61. The method of claim 59 which includes determining an arithmetic weighting factor in accordance with the period in the menstrual cycle of the human female subject and applying the arithmetic weighting factor to said first biopotential value.

62. The method of claim 59 which includes determining an arithmetic weighting factor in accordance with the time of day during which said test period occurs and applying said arithmetic weighting factor to said first biopotential value.

63. A noninvasive method for sensing and processing biopotentials from a lesion containing first quadrant of a symptomatic breast of a human female subject using a plurality of spaced biopotential sensors which includes arranging at least one reference sensor in contact with a skin surface of said subject, arranging a plurality of test sensors with at least a first of said test sensors in contact with a skin surface of the subject over said lesion, at least a second test sensor in contact with a skin surface of said subject in a second quadrant of the symptomatic breast which is outside said first quadrant, at least a third test sensor in contact with a skin surface in a third quadrant of said quadrants of said symptomatic breast which is outside said first and second quadrants, and at least a fourth test sensor in contact with a skin surface in a fourth quadrant of the symptomatic breast which is outside said first, second and third quadrants, obtaining during a test period a first biopotential value using a reference sensor and said first test sensor to provide a first variable, using said reference sensor and second test sensor during the test period to obtain a second biopotential value, using said reference sensor and third test sensor during the test period to obtain a third biopotential value, using said reference sensor and fourth test sensor during the test period to obtain a fourth biopotential value, obtaining a median value of the sum of said second, third and fourth biopotential values as a second variable, and subtracting said second variable from said first variable to provide a first differential value.

64. The method of claim 63 which includes taking a plurality of biopotential measurements with said reference sensor and said second test sensor during said test period to obtain a second plurality of measurement values, taking a plurality of biopotential measurements with said reference sensor and said third test sensor during said test period to obtain a third plurality of measurement values, taking a plurality of biopotential measurements with said reference sensor and said fourth test sensor during said test period to obtain a fourth plurality of measurement values, averaging said second plurality of measurement values to obtain a second average value as said second biopotential value, averaging said third plurality of measurement values to obtain a third average value as said third biopotential value, and averaging said fourth plurality of measurement values to obtain a fourth average value as said fourth biopotential value.

65. The method of claim 64 which includes taking a plurality of biopotential measurements with said reference sensor and first test sensor during a test period to obtain a first plurality of measurement values, and averaging said first plurality of measurement values to obtain a first average value as said first variable.

66. The method of claim 65 which includes taking the same number of biopotential measurements with said first, second, third and fourth test sensors during a test period.

67. The method of claim 66 which includes comparing said first differential value to a predetermined reference value to determine a relationship therebetween.

68. The method of claim 63 which includes placing at least a fifth, sixth, seventh and eighth test sensor in contact with the skin surface of an asymptomatic breast in positions on the asymptomatic breast corresponding to the location of the first, second, third and fourth sensors respectively on the symptomatic breast, using a reference sensor and said fifth, sixth, seventh and eighth test sensors during a test period to obtain fifth, sixth, seventh and eighth biopotential values respectively, obtaining a second mean value from the sum of of said fifth, sixth, seventh and eighth biopotential values, and adding said second mean value to said first differential value to obtain a final differential value.

69. The method of claim 68 which includes comparing said final differential value to a predetermined reference value to determine a relationship therebetween.

70. The method of claim 69 which includes determining an arithmetic weighting factor in accordance with the age of the human female subject and applying the arithmetic weighting factor to said first biopotential value.

71. The method of claim 69 which includes determining an arithmetic weighting factor in accordance with the period in the menstrual cycle of the human female subject and applying the arithmetic weighting factor to said first biopotential value.

72. The method of claim 69 which includes determining an arithmetic weighting factor in accordance with the time of day during which said test period occurs and applying said arithmetic weighting factor to said first biopotential value.

73. An apparatus for sensing and processing electropotentials from the symptomatic breast of a human female subject which includes a lesion containing quadrant and a plurality of non-lesion containing quadrants comprising:
at least one DC biopotential reference sensor for contacting the female subject at a reference location,
at least one DC biopotential test sensor for contacting the symptomatic breast and operating with a reference sensor during a test period to detect electropotentials and to provide output test potentials, one of said at least one test sensors forming a lesion test sensor for contact with a skin surface of the symptomatic breast over the lesion in the lesion containing quadrant,
a signal processing section connected to receive the output test potentials provided by said reference sensor and lesion test sensor, said signal processing section including a processor for obtaining a first variable from said output test potentials provided by said reference sensor and lesion test sensor, a storage unit which stores at least one group of physiological weighting factor values which vary in value in accordance with physiological data indicative of at least one physiological factor present in the female subject, and an input unit for inputting physiological data relative to a human female subject under test to said processor, said processor operating in response to such physiological data to select a stored physiological weighting factor value determined by said physiological data and to apply said stored physiological weighting factor value to said variable.

74. The apparatus of claim 73 wherein said processor operates to sample and receive a first plurality of output test potentials from said reference sensor and lesion test sensor during a test period and to average said first plurality of output test potentials to obtain a first average value as said first variable.

75. The apparatus of claim 74 wherein said storage unit stores a plurality of different physiological weighting factor values which vary in value in accordance with different physiological data indicative of a plurality of different physiological factors present in the female subject, said processor operating in response to each type of physiological data provided by said input unit to select a stored physiological weighting factor value determined by each type of physiological data from said input unit and to apply each such physiological weighting factor value to said first variable.

76. The apparatus of claim 74 which includes at least two DC biopotential test sensors for contacting the symptomatic breast and each operating with a reference sensor during a test period to detect electropotentials and to provide output test potentials, one of said test sensors forming a first non-lesion test sensor for contact with a skin surface of the symptomatic breast in a first non-lesion quadrant separate from said lesion quadrant, said processor operating to sample and receive a second plurality of output test potentials from said reference sensor and first non-lesion test sensor during said test period and to average said second plurality of output test potentials to obtain a second average value as a second variable, said processor operating to subtract said second variable from said first variable.

77. The apparatus of claim 76 wherein said processing section includes a storage unit for storing a plurality of weighting factor values including a first arithmetic weighting factor value and a second arithmetic weighting factor value, said processor operating to retrieve and apply said first weighting factor value to said first average value and said second weighting factor value to said second average value before subtracting said second variable from said first variable.

78. The apparatus of claim 77 wherein said first stored arithmetic weighting factor value is greater than said second stored weighting factor value.

79. The apparatus of claim 76 wherein said processing section includes a storage unit which stores menstrual cycle weighting factor values which vary in value in accordance with the period in the menstrual cycle of a human female subject and an input unit for inputting the period in the menstrual cycle of a human female subject under test, said processor operating in response to a menstrual cycle period input from said input unit to select a stored menstrual cycle weighting factor value and to apply said menstrual cycle weighting factor value to said first average value before subtracting said second variable from said first variable.

80. The apparatus of claim 76 wherein said processing section includes a storage unit which stores age weighting factor values which vary in value in accordance with the age of a human female subject and an input unit for inputting the age of a human female subject under test, said processor operating in response to an age input from said input unit to select a stored age weighting factor value and to apply said age weighting factor value to said first average value before subtracting said second variable from said first variable.

81. The apparatus of claim 76 wherein said processing section includes a storage unit which stores time of day weighting factor values which vary in value in accordance with the time of day during which a test period occurs, and an input unit for inputting the time of day when the test period is to occur, said processor operating in response to a time of day input from said input unit to select a stored time of day weighting factor value and to apply said time of day weighting factor value to said first average value before subtracting said second variable from said first variable.

82. An apparatus for screening four quadrants of a first breast of a human female subject to identify a lesion containing quadrant and non-lesion containing quadrants by sensing and processing electropotentials therefrom comprising:
at least one DC biopotential reference sensor for contacting the female subject at a reference location, at least one DC biopotential test sensor for contacting the first breast in each quadrant thereof, each test sensor operating with a reference sensor during a screening period to form a reference-test sensor combination to detect electropotentials and provide output screening potentials, and a signal processing section connected to separately receive the output screening potentials provided by each said reference-test sensor combination during a screening period; said signal processing section including a processor to separately receive the output screening potentials for each quadrant of the first breast and to obtain therefrom a quadrant signal value, said processor operating to compare said quadrant signal values to identify as a lesion quadrant any quadrant having a quadrant signal value which differs more than a predetermined amount from the signal values of the remaining quadrants, the remaining quadrants being identified by said processor as non-lesion quadrants.

83. The apparatus of claim 82 wherein said processor operates to sample and receive a plurality of output screening potentials from each of said reference-test sensor combinations during a screening period and to average the output screening potentials for each said reference-test sensor combination in each quadrant of the first breast to obtain a quadrant signal value for each quadrant of the first breast.

84. The apparatus of claim 83 wherein said processor operates to average the quadrant signal values to obtain a breast average signal value and to compare each quadrant signal value to the breast average signal value to identify as a lesion quadrant any quadrant having a quadrant signal value which differs more than a predetermined amount from the breast average signal value.

85. An apparatus for sensing and processing electropotentials from four quadrants of a first breast and a nipple of said first breast for a human female subject comprising:

at least one DC biopotential reference sensor for contacting the female subject at a reference location, a DC biopotential nipple sensor for contacting the nipple of said first breast and operating with said reference sensor during a test period to detect electropotentials and provide output nipple potentials, at least one DC biopotential test sensor for contacting the first breast in each quadrant thereof, each test sensor operating with said reference sensor during a test period to provide at least one reference-test sensor combination for each breast quadrant, and to detect electropotentials and provide output test potentials, and a signal processing section connected to separately receive the output nipple potentials and output test potentials, said processing section including a processor for obtaining a first variable from said output nipple potentials and operating to arithmetically combine all of said output test potentials and to obtain a second variable from the combination of all of said output test potentials, the processor operating to subtract the second variable from the first variable to obtain a first differential value.

86. The apparatus of claim 85 wherein said processor operates to sample and receive a first plurality of nipple output potentials during a test period and to average said plurality of nipple output potentials to obtain a first average value as said first variable, and to sample and receive a first plurality of output test potentials from at least one reference-test sensor combination in a first breast quadrant of the first breast, a second plurality of output test potentials from at least one reference-test sensor combination in a second breast quadrant of the first breast, a third plurality of output test potentials from at least one reference-test sensor combination in a third breast quadrant of the first breast and a fourth plurality of output test potentials from at least one reference-test sensor combination in a fourth quadrant of the first breast, said processor operating to obtain a first average value from said first plurality of output test potentials, a second average value from said second plurality of output test potentials, a third average value from said third plurality of output test potentials and a fourth average value from said fourth plurality of output test potentials and to use said first, second, third and fourth average values to obtain said second variable.

87. An apparatus for sensing and processing electropotentials from a test site on the skin of a human subject comprising at least one DC biopotential reference sensor for contacting the subject at a reference location, a plurality of DC biopotential test sensors for contacting the subject at spaced locations at the test site, each said test sensor operating with a reference sensor to form a reference-test sensor combination to detect electropotentials and to provide output test potentials during a test period, at least one analog to digital converter connected to separately receive the output test potentials from each reference-test sensor combination during a test period and operating to convert said output test potentials from each reference-test sensor combination to digital test signals for said reference-test sensor combination, and a signal processing section connected to separately receive the output test potentials from each reference-test sensor combination, said signal processing section including a processor connected to separately receive the digital test signals for each said reference-test sensor combination from said analog to digital converter, and to obtain therefrom a separate digital test signal value for each said reference-test sensor combination, and a storage unit which stores a plurality of physiological weighting factor values representative of a factor having a physiological effect on said human subject connected to said processor, said processor operating at the end of a test period to combine said digital test signal values to identify at least one potential difference relationship therebetween, said processor operating to apply at least one physiological weighting factor value to said digital test signal values before arithmetically combining said digital test signal values.

88. The apparatus of claim 87 wherein said processing section includes an input unit for inputting the age of a human subject under test to said processor, said storage unit storing age weighting factor values which vary in value in accordance with age, said processor operating in response to an age input from said input unit to select a stored age weighting factor value and to apply said age weighting factor value to said digital test signal values.

89. The apparatus of claim 88 wherein said input unit operates to input the time of day when the test period is to occur and said storage unit stores time of day weighting factor values which vary in value in accordance with the time of day during which a test period occurs, said processor operating in response to a time of day input from said input unit to select a stored time of day weighting factor value and to apply said time of day weighting factor value to said digital test signal values.

90. The apparatus of claim 87 wherein said human subject is a female subject, said processing unit including an input unit for inputting the period in the menstrual cycle of a human female subject under test, said storage unit storing menstrual cycle weighting factor values which vary in value in accordance with the period in the menstrual cycle of a human female subject, said processor operating in response to a menstrual cycle period input from said input unit to select a stored menstrual cycle weighting factor value and to apply said menstrual cycle weighting factor value to said digital test signal values.

91. The apparatus of claim 90 wherein said input unit operates to input the time of day when the test period is to occur and said storage unit stores time of day weighting factor values which vary in value in accordance with the time of day during which a test period occurs, said processor operating in response to a time of day input from said input unit to select a stored time of day weighting factor value and to apply said time of day weighting factor value to said digital test signal values.

92. The apparatus of claim 90 wherein said input unit operates to input the age of a human subject under test to said processor, said storage unit storing age weighting factor values which vary in value in accordance with age, said processor operating in response to an age input from said input until to select a stored age weighting factor value and to apply weighting factor value and to apply said age weighting factor value to said digital test signal values.

93. The apparatus of claim 92 wherein said input unit operates to input the time of day when the test period is to occur and said storage unit stores time of day weighting factor values which vary in value in accordance with the time of day during which a test period occurs, said processor operating in response to a time of day input from said input unit to select a stored time of day weighting factor value and to apply said time of day weighting factor value to said digital test signal values.

94. The apparatus of claim 87 wherein said processing unit includes an input unit for inputting the time of day when the test period is to occur, said storage unit storing time of day weighting factor values which vary in value in accordance with the time of day during which a test period occurs, said processor operating in response to a time of day input from said input unit to select a stored time of day weighting factor value and to apply said time of day weighting factor value to said digital test signal values.

95. A method for approximating a gradient around a lesion on the symptomatic breast of a human female subject using a plurality of spaced biopotential sensors which include at least one reference sensor and at least five test sensors the method including positioning the reference sensor in contact with a skin surface of a subject, positioning a first of the test sensors in contact with the skin surface of the subject over said lesion, positioning the remaining second, third, fourth and fifth test sensors in spaced relationship in a circle around said first test sensor with said first sensor being positioned in the center of said circle, obtaining during a test period a first biopotential value using the reference sensor and said first test sensor, obtaining during the test period a second biopotential value using the reference sensor and the second test sensor, a third biopotential value using the reference sensor and the third test sensor, a fourth biopotential value using the reference sensor and the fourth test sensor and a fifth biopotential value using the reference sensor and the fifth test sensor and subtracting from first biopotential value a value equal to one fourth the sum of the second, third, fourth and fifth biopotential values.

* * * * *